United States Patent
Miller et al.

(10) Patent No.: US 8,853,148 B2
(45) Date of Patent: Oct. 7, 2014

(54) COMPOSITIONS FOR MASKING THE FLAVOR OF NUTRIENTS AND METHODS FOR MAKING SAME

(75) Inventors: Kevin Burke Miller, Minneapolis, MN (US); Candis Diane Kvamme, Brooklyn Park, MN (US); Trent Stellingwerff, Victoria (CA); Lionel Jean Rene Bovetto, Larringes (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/583,712

(22) PCT Filed: Mar. 9, 2011

(86) PCT No.: PCT/US2011/027714
§ 371 (c)(1),
(2), (4) Date: Oct. 22, 2012

(87) PCT Pub. No.: WO2011/112695
PCT Pub. Date: Sep. 15, 2011

(65) Prior Publication Data
US 2013/0065822 A1    Mar. 14, 2013

Related U.S. Application Data

(60) Provisional application No. 61/313,348, filed on Mar. 12, 2010, provisional application No. 61/447,148, filed on Feb. 28, 2011.

(51) Int. Cl.

| | | |
|---|---|---|
| A61K 38/00 | (2006.01) | |
| A61P 3/02 | (2006.01) | |
| C07K 2/00 | (2006.01) | |
| A23C 21/10 | (2006.01) | |
| A23L 1/305 | (2006.01) | |
| A23C 21/08 | (2006.01) | |
| A23C 11/04 | (2006.01) | |
| A23L 1/00 | (2006.01) | |
| A23L 1/304 | (2006.01) | |
| A23L 1/22 | (2006.01) | |
| A23C 9/152 | (2006.01) | |
| A23L 1/30 | (2006.01) | |
| A23L 1/39 | (2006.01) | |
| A23L 2/02 | (2006.01) | |
| A23L 2/38 | (2006.01) | |
| A23L 1/24 | (2006.01) | |
| A61K 38/17 | (2006.01) | |
| A23L 1/01 | (2006.01) | |
| A61K 31/198 | (2006.01) | |
| A23L 3/46 | (2006.01) | |
| A23L 1/302 | (2006.01) | |
| A23C 21/06 | (2006.01) | |
| A23C 21/02 | (2006.01) | |
| A23L 1/303 | (2006.01) | |
| A23L 3/44 | (2006.01) | |

(52) U.S. Cl.
CPC ............... *A23L 1/3056* (2013.01); *A23C 21/10* (2013.01); *A23L 1/3051* (2013.01); *A23C 21/08* (2013.01); *A23C 11/04* (2013.01); *A23L 1/0002* (2013.01); *A23L 1/304* (2013.01); *A23V 2002/00* (2013.01); *A23L 1/22075* (2013.01); *A23C 9/1526* (2013.01); *A23L 1/305* (2013.01); *A23L 1/3014* (2013.01); *A23L 1/39* (2013.01); *A23L 2/02* (2013.01); *A23L 2/38* (2013.01); *A23L 1/246* (2013.01); *A61K 38/1722* (2013.01); *A23L 1/0128* (2013.01); *A61K 31/198* (2013.01); *A23L 2/382* (2013.01); *A23L 3/46* (2013.01); *A23L 1/30* (2013.01); *A23L 1/302* (2013.01); *A23C 21/06* (2013.01); *A23C 21/026* (2013.01); *A23L 1/303* (2013.01); *A23L 3/44* (2013.01)
USPC ............................................. 514/1.1; 514/5.6

(58) Field of Classification Search
None
See application file for complete search history.

(56) References Cited

U.S. PATENT DOCUMENTS

2009/0035437 A1 *    2/2009    Bovetto et al. ................ 426/588

FOREIGN PATENT DOCUMENTS

| WO | 0230417 | 4/2002 |
|---|---|---|
| WO | WO 2007/122613 | * 11/2007 |
| WO | 2010002242 | 1/2010 |

OTHER PUBLICATIONS

Kimball, Signaling Pathways and Molecular Mechanisms through which Branched-Chain Amino Acids Mediate Translational Control of Protein Synthesis, J. Nutr. 136: 227S-231S, 2006.*
Maehashi et al, Bitter peptides activate hTAS2Rs, the human bitter receptors, Biochem Biophys Res Commun. Jan. 25, 2008; 365(4): 851-855.*
International Search Report, PCT/US2011/027714—mailing date May 30, 2011—3 pages.
Written Opinion, PCT/US2011/027714—mailing date May 30, 2011—5 pages.

* cited by examiner

*Primary Examiner* — Marcela M Cordero Garcia
*Assistant Examiner* — Sergio Coffa
(74) *Attorney, Agent, or Firm* — K&L Gates LLP

(57) ABSTRACT

Nutritional compositions and methods of making and using the nutritional compositions are provided. In a general embodiment, the present disclosure provides nutritional compositions having whey protein micelles and leucine. The nutritional compositions provide a sufficient amount of leucine to improve protein synthesis in humans, while also maintaining a low-viscosity fluid matrix and acceptable organoleptic properties.

10 Claims, 2 Drawing Sheets

COMPOSITIONS FOR MASKING THE FLAVOR OF NUTRIENTS AND METHODS FOR MAKING SAME

CROSS REFERENCE TO RELATED APPLICATIONS

The present application is a National Stage of International Application No. PCT/US2011/027714, filed on Mar. 9, 2011, which claims priority to U.S. Provisional Application No. 61/313,348, filed on Mar. 12, 2010, and U.S. Provisional Application No. 61/447,148, filed on Feb. 28, 2011, the entire contents of which are being incorporated herein by reference.

BACKGROUND

The present disclosure generally relates to health and nutrition. More specifically, the present disclosure relates to nutritional compositions having whey protein micelles and at least one amino acid, and methods of making and using the nutritional compositions to optimize the flavor profile and physical properties of the compositions to provide improved patient health.

There are many types of nutritional compositions currently on the market. Nutritional compositions can be targeted toward certain consumer types, for example, young, elderly, athletic, etc., based on the specific ingredients of the nutritional composition. Nutritional compositions can also be formulated based on the certain physiological conditions that the nutritional compositions are intended to treat or improve, or may be based on desired physical or organoleptic properties of the nutritional compositions.

One goal of nutritional support is to increase the amounts of nutrients provided in nutritional compositions to provide a consumer with a sufficient amount of the nutrient to achieve a specific biological result. However, many nutrients that are used in nutritional compositions to provide a specific nutritional benefit to a consumer instead impart an undesirable taste or odor to the composition making it unappealing for consumption. As a result, the desired biological result is not achieved when the consumer refuses to ingest the composition due to its poor organoleptic properties. Thus, it is desired to provide nutritional compositions having increased amounts of nutrients while at the same time providing tolerable physical and organoleptic properties.

SUMMARY

Nutritional compositions and methods of making and using the nutritional compositions are provided. In a general embodiment, the present disclosure provides nutritional compositions having whey protein micelles and leucine. The nutritional compositions provide a sufficient amount of leucine to improve protein synthesis in humans, while also maintaining a low-viscosity fluid matrix and acceptable organoleptic properties.

In an embodiment, a nutritional composition is provided and includes whey protein powder comprising whey protein micelles, and leucine, wherein the total leucine in the composition comprises between 20% and 40% by weight dry matter.

In another embodiment, a nutritional composition is provided and includes whey protein powder having whey protein micelles, and added leucine, wherein the dry weight ratio of added leucine to whey protein micelles is from about 1:2 to about 1:3.

In an embodiment, the dry weight ratio of added leucine to whey protein micelles is about 1:2.6.

In an embodiment, the whey protein powder includes at least about 20% whey protein micelles. The whey protein may also include at least 50% whey protein micelles. The whey protein may also include at least 80% whey protein micelles.

In an embodiment, the composition is a powder composition.

In an embodiment, the whey protein powder is obtained by spray-drying or freeze-drying a whey protein micelles concentrate.

In an embodiment, the whey protein powder has a water binding capacity of at least 50%. The whey protein powder may also have a water binding capacity of at least 90%. The whey protein powder may also have a water binding capacity of at least 100%.

In an embodiment, the whey protein powder has a glycerol binding capacity of at least 50%.

In an embodiment, the whey protein powder has an ethanol binding capacity of at least 50%.

In an embodiment, the whey protein powder has an oil binding capacity of at least 30%.

In an embodiment, the whey protein powder is filled with the leucine.

In an embodiment, the whey protein powder includes whey protein micelles and leucine in a weight ratio of about 30:1 to about 1:100.

In an embodiment, the whey protein powder is obtained by a process of spray-drying or freeze-drying that is performed with the leucine.

In an embodiment, the whey protein powder has an angle of repose less than 35°.

In an embodiment, the whey protein powder is prepared so as to function as a flowing agent.

In an embodiment, the whey protein micelles have a size of less than 1 micron.

In an embodiment, the whey protein micelles are coated with a coating. The coating may be selected from the group consisting of an emulsifier, a protein, a peptide, a protein hydrolysate, a gum, or combinations thereof. The protein may be selected from the group consisting of protamine, lactoferrin, rice proteins, or combinations thereof. The protein hydrolysate may be a hydrolysate selected from the group consisting of from protamine, lactoferrin, rice, casein, whey, wheat, soy protein, or combinations thereof. The emulsifier may be selected from the group consisting of sulfated butyl oleate, diacetyltartaric acid esters of mono- and diglycerides, citric acid esters of monoglycerides, stearoyl lactylates, or combinations thereof.

In an embodiment, the composition is a source of complete nutrition. Alternatively, the composition may be a source of incomplete nutrition. The composition may also be a tube feed composition, or may be used for short term administration or long term administration.

In an embodiment, the composition may include an antioxidant selected from the group consisting of beta-carotene, vitamin C, vitamin E, selenium, or combinations thereof.

In an embodiment, the composition may include a vitamin selected from the group consisting of vitamin A, vitamin B1, vitamin B2, vitamin B3, vitamin B5, vitamin B6, vitamin B7, vitamin B9, and vitamin B12, vitamin C, vitamin D, vitamin E, vitamin K, folic acid, biotin, or combinations thereof.

In an embodiment, the composition may include a mineral selected from the group consisting of boron, calcium, chromium, copper, iodine, iron, magnesium, manganese, molybdenum, nickel, phosphorus, potassium, selenium, silicon, tin, vanadium, zinc, or combinations thereof.

In yet another embodiment, a nutritional composition is provided and includes whey protein micelles, leucine, and a liquid, wherein the total amount of leucine in the composition is less than about 2.5 g per 100 g of the liquid.

In an embodiment, the leucine is present in an amount from about 1 g to about 2 g.

In still yet another embodiment, a nutritional composition is provided and includes whey protein micelles, and leucine, wherein the total amount of leucine in the composition is less than about 25 g per 1 liter of a liquid.

In an embodiment, the liquid is selected from the group consisting of water, water-based beverages, fruit juice, milk, or combinations thereof.

In an embodiment, the leucine is present in an amount of about 24 g.

In an embodiment, the composition is a tube feed composition.

In another embodiment, a nutritional composition is provided and includes whey protein powder comprising whey protein micelles and added leucine, wherein the total dry weight of the added leucine is about 30% to about 40% of the total dry weight of the whey protein micelles.

In an embodiment, the total dry weight of the added leucine is about 37% of the total dry weight of the whey protein micelles.

In an embodiment, the composition is a powder composition.

In an embodiment, the whey protein micelles are spherical agglomerates of denatured whey protein. The whey proteins may be arranged in such a way that the hydrophilic parts of the proteins are oriented toward an outer part of the agglomerate and the hydrophobic parts of the protein are oriented toward an inner core of said micelle.

In yet another embodiment, a process for the production of a whey protein micelles concentrate is provided. The process includes the steps of (a) adjusting the pH of a whey protein aqueous solution to a value between 3.0 and 8.0, (b) subjecting the aqueous solution to a temperature of between 70 and 95° C., (c) concentrating a dispersion obtained in step (b), (d) adding leucine to the dispersion, and (e) spray drying or freeze drying the whey protein micelles concentrate with leucine. The step of (a) adjusting is completely very precisely such that the pH is adjusted to ±0.05 pH units.

In an embodiment, the mineral content of the whey protein solution is less than 2.5%. The whey protein may also be demineralized.

In an embodiment, the pH of the whey protein solution is adjusted to between 5.8 and 6.6. The pH may also be adjusted to between 3.8 and 4.5.

In an embodiment, the concentration of the whey protein aqueous solution is less than 12%. The concentration may also be less than 4%.

In an embodiment, the heating is carried out for a time of 10 seconds to 2 hours. The aqueous solution may also be heated for a time of 15 minutes. The heating may be performed by microwaves.

In an embodiment, the yield of micelles before concentration is at least 35%. The yield of micelles before concentration may also be at least 50%. The yield of micelles before concentration may also be at least 80%.

In an embodiment, the micelles have an average size of less than 1 micron. The micelles may have an average size of 100-900 nm. The proportion of micelles with an average size of between 100 nm and 700 nm may be greater than 80%.

In an embodiment, the concentration is performed by a method selected from the group consisting of evaporation, centrifugation, sedimentation, ultrafiltration, microfiltration, or combinations thereof. The centrifugation may be performed after acidification to a pH of 4.5. The spontaneous sedimentation may be performed at a pH of 4.5. The sedimentation time may be greater than 12 hours.

In still yet another embodiment, a method for preparing a nutritional product is provided. The method includes the steps of (a) adjusting the pH of a whey protein aqueous solution to a value between 3.0 and 8.0, (b) subjecting the aqueous solution to a temperature of between 70 and 95° C., (c) concentrating a dispersion obtained in step (b), (d) adding leucine to the dispersion, (e) spray drying or freeze drying the whey protein micelles concentrate with leucine, and (f) adding the dried whey protein micelles concentrate with leucine to a composition to prepare the product.

In another embodiment, a method for the production of a consumable product is provided and includes mixing whey protein micelles, a concentrate thereof or a powder thereof with added leucine to create a mixture and processing the mixture to form a consumable product. The total amount of leucine in the consumable product is between 20% and 40% by weight of dry matter. The processing may include subjecting the mixture to heat, to pressure, to acidic or basic conditions, to shear, to cooling, or combinations thereof.

In still yet another embodiment, a method for the production of a consumable product is provided and includes co-drying a whey protein micelle solution or concentrate with added leucine to form a powder having dry weight ratio of added leucine to whey protein micelles from about 1:2 to about 1:3 and adding the powder to the product. The co-drying is selected from the group consisting of spray drying, freeze drying, or combinations thereof.

In another embodiment, a method of masking off-flavors of a nutrient in a composition is provided. The method includes the steps of mixing a whey protein micelle powder and up to 2.5 g of added leucine to form a mixture and adding the mixture to 100 g of a liquid carrier to form a composition.

An advantage of the present disclosure is to provide improved nutritional compositions.

Another advantage of the present disclosure is to provide nutritional compositions having increased amounts of nutrients.

Yet another advantage of the present disclosure is to provide nutritional compositions that provide acceptable organoleptic properties.

Still yet another advantage of the present disclosure is to provide nutritional compositions that provide acceptable physical characteristics.

Another advantage of the present disclosure is to provide nutritional compositions with low viscosities.

An advantage of the present disclosure is to provide nutritional compositions that stimulate protein synthesis in humans.

Yet another advantage of the present disclosure is to provide nutritional compositions that promote muscle growth.

Still yet another advantage of the present disclosure is to provide nutritional compositions that mask off-flavors of nutrients in the nutritional composition.

Another advantage of the present disclosure is to provide methods for making compositions including increased amounts of nutrients.

Yet another advantage of the present disclosure is to provide methods of administering a nutritional composition.

Additional features and advantages are described herein, and will be apparent from the following Detailed Description.

DETAILED DESCRIPTION

Figure 1:
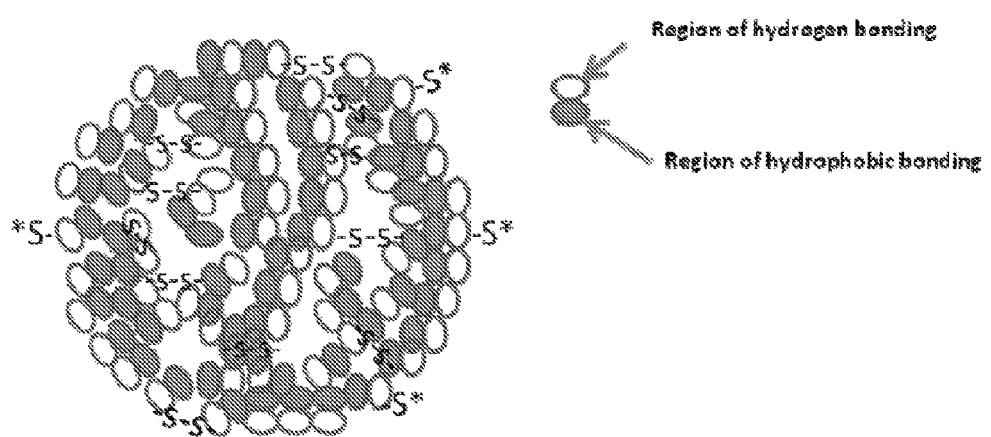
FIG. 1 shows a highly schematic structure of a whey protein micelle in accordance with an embodiment of the present disclosure.

As used herein, "about," is preferably understood to refer to numbers in a range of numerals. Moreover, all numerical ranges herein should be understood to include all integer, whole or fractions, within the range.

As used herein, "effective amount" is preferably an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

As used herein, the terms "treatment," "treat" and "to alleviate" is related preferably to both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition As used herein the term "patient" is preferably understood to include an animal, especially a mammal, and more especially a human that is receiving, could benefit from, or intended to receive treatment, as it is herein defined.

As used herein, "animals" includes, but is not limited to mammals which includes but is not limited to rodents, aquatic mammals, domestic animals such as dogs and cats, farm animals such as sheep, pigs, cows and horses, and humans. Wherein the terms animal or mammal or their plurals are used, it is contemplated that it also applies to any animals that are capable of the effect exhibited or intended to be exhibited by the context of the passage.

As used herein, "mammal" includes but is not limited to rodents, aquatic mammals, domestic animals such as dogs and cats, farm animals such as sheep, pigs, cows and horses, and humans. Wherein the term mammal is used, it is contemplated that it also applies to other animals that are capable of the effect exhibited or intended to be exhibited by the mammal.

The term "protein," "peptide," "oligopeptides" or "polypeptide" as used herein is preferably understood to refer to any composition that includes, two or more amino acids joined together by a peptide bond (dipeptide, tripeptide, or polypeptide), collagen, precursor, homolog, analog, mimetic, salt, prodrug, metabolite, or fragment thereof or combination. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a polyphenol, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol (GPI) membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins," which refers to linear or non-linear polypeptides, consisting of alternating repeats of a peptide.

Nutritional products and compositions are preferably understood to further include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamin. The optional ingredients can be added in any suitable amount.

For example, compositions and products of the present disclosure may also include, for example, antioxidants, vitamins and minerals. As used herein the term "antioxidant" is preferably understood to include any one or more of various substances (as beta-carotene (a vitamin A precursor), vitamin C, vitamin E, and selenium) that inhibit oxidation or reactions promoted by Reactive Oxygen Species (ROS) and other radical and non-radical species. Additionally, antioxidants are molecules capable of slowing or preventing the oxidation of other molecules.

As used herein the term "vitamin" is preferably understood to include any of various fat-soluble or water-soluble organic substances essential in minute amounts for normal growth and activity of the body and obtained naturally from plant and animal foods or synthetically made, pro-vitamins, derivatives, analogs. Non-limiting examples of vitamins include vitamin A, vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid), and vitamin B12 (various cobalamins; commonly cyanocobalamin in vitamin supplements), vitamin C, vitamin D, vitamin E, vitamin K, folic acid and biotin.

As used herein the term "minerals" is preferably understood to include boron, calcium, chromium, copper, iodine, iron, magnesium, manganese, molybdenum, nickel, phosphorus, potassium, selenium, silicon, tin, vanadium, zinc, and combinations thereof.

Whey protein micelles are spherical (regular shape close to natural casein micelles) mono-dispersed micro-gels obtained by auto assembling of native whey proteins during heat treatment at a very specific pH. Whey protein micelles have unique characteristics and properties including, for example, a narrow size distribution with a diameter between 100 and 900 nm and a polydispersity index below 0.2, a turbidity value measured at 500 nm (between 20 and 50 absorbance units for a 4% protein solution) that is stable for 10 minutes, and a spherical shape as imaged by TEM microscopy.

The final architecture of whey protein micelle aggregates confers properties like emulsification, micellar casein substitution, whitening, foaming, texturising and/or of filling agents. The whey protein micelles are microgels of 30% whey protein concentration with unique physical characteristics (size, charge, density, size distribution) conferring exceptional including, for example, stable to salt addition, low viscosity at high concentration, gelling between pH 4 and 5 and with high stability against heat treatment used for pasteurization or sterilisation.

Whey protein micelles are obtained by heat treatment of native whey protein solutions adjusted at a very specific and precise pH at which the net (negative or positive) charge, induced this specific aggregation by auto-assembling. These aggregates are in a particular organised state that results from a balance between repulsive and attractive electrostatic forces associated to hydrophobic interactions and to an asymmetric repartition of charges present at the surface of the proteins. This phenomena occurred below and above 0.7 pH unit of the iso-electric point (i.e., pH 4.3 and 5.8 for IEP of 5.1) for pure beta-lactoglobulin.

Micellisation does not occur at room temperature because whey protein hydrophobicity is buried into native protein structure. To induce micellisation (formation of spherical mono dispersed protein micro gel by auto-assembling), a protein conformational modification is needed. This modification is induced by heat treatment; during the first early stage of micelle formation. This auto assembling phenomena is reversible by acidification at pH 2.0 just after the optimal temperature was reached (i.e., 85° C.). This very acidic pH block thiol/disulfide interchanges and the non stabilised micelle structure is rapidly dismantle. In normal conditions, without post acidification at pH 2.0, due to thiol activation by the heat treatment, a fast cross linking stabilised the micelle during the incubation at constant temperature (15 min at 85° C.), this incubation time could be prolonged up to 45 min or 120 min. After this incubation, micellisation is not spontaneously reversible. Dissociating agent and reducing agent are needed to recover protein units.

Whey protein is one of the most abundant natural sources of the branched-chain amino acids (leucine, isoleucine and valine). Because the nutritional profile of whey protein is among the best sources for such amino acids it is very desirable for use in nutritional compositions. More specifically, whey protein micelles, which are the product of technologies described in patent applications to Nestec S.A., allow whey protein to be concentrated beyond what is typically feasible using standard methods of processing, yet remain in a liquid form. The pending patent applications to Nestec S.A. that describe such whey protein micelle technologies include International Application PCT/EP2007/052877, filed Mar. 26, 2007; International Application PCT/EP2007/052900, filed Mar. 27, 2007; and U.S. Ser. No. 12/280,244, filed Aug. 21, 2008, the entire contents of which are included herein by reference. One benefit afforded by the micelles manufactured by the technologies described in the above-mentioned processes is that whey protein can be included at large concentrations, but retain a low-viscosity fluid matrix.

Additionally, the amino acid profile of the source whey protein is also maintained during the manufacturing processes described in the above-identified applications, which provides the same nutritional value as whey. Branched-chain amino acids are those amino acids that have aliphatic side-chains that are non-linear. The combination of these three essential amino acids makes up approximately ⅓ of skeletal muscle in the human body, and plays an important role in protein synthesis. Branched-chain amino acids may also be used to aid in the recovery of burn victims, as well as for supplementation for strength athletes.

Because leucine, isoleucine and valine are essential amino acids, these amino acids cannot be synthesized by the body and, thus, must be ingested. As a dietary supplement, leucine has been found to slow the degradation of muscle tissue by increasing the synthesis of muscle proteins in aged rats. Whey protein is among the richest natural sources of leucine (12-15% by weight of the total amino acids), including about 1 g of leucine per 10 g of whey protein micelles in the whey protein. However, the amount of leucine necessary to significantly improve protein synthesis in humans is reported to be approximately 3 g or more delivered in a bolus serving. As a result, it is necessary to provide more than 30 g of whey protein to achieve 3 g of leucine. However, the flavor of leucine is typically unpleasant when included in doses that are efficacious in the stimulation of protein synthesis in humans. Indeed, the sensory properties of leucine include a bitter mouth taste that is unpleasant to consumers.

As such, oral nutritional products have been limited in their ability to deliver efficacious amounts of branch chain amino acids because of the flavor profile. In addition, whey protein has the habit of gellification when heated in neutral pH conditions. Therefore, the beverage applications for branch chain amino acids are extremely limited. Further, tablet and pill delivery of branch chain amino acids is also not convenient as a result of the dose to be administered (3+ g at a time).

Applicants have surprisingly found that it is possible to combine whey protein micelles with the free amino acid leucine to create compositions (e.g., a beverage) for the purpose of supporting muscle growth. Specifically, the compositions include whey protein micelles and a significant amount of leucine, but do not have bitter or off-flavors that are typically associated with doses of leucine that are efficacious in the stimulation of protein synthesis in humans. Applicants have surprisingly found, therefore, that whey protein micelles can be utilized as a mask to offset the bitterness of off-flavor amino acids in beverages and other oral nutritional products. Although the present disclosure refers to the use of whey protein micelles and leucine, the skilled artisan will immediately appreciate that other branch chain amino acids such as isoleucine and valine may also be employed in similar uses.

Indeed, Applicants have found that the combination of whey protein micelles and leucine can be incorporated into nutritional compositions (e.g., beverages) at concentrations of both the whey protein and supplemental leucine that deliver a benefit to the consumer without the sensory limitations previously encountered. For example, prior art beverages are either limited by the inclusion of whey protein, which provides unacceptable viscosity, or leucine, which provides unacceptable organoleptics. At least these two limitations are solved by the combination of the micellar protein with the challenging nutrient. Without wishing to be bound to any theory, it is believed that the structure of the protein micelles and their interaction with the leucine (or other off-flavor nutrients) prevents the unpleasant bitterness perception by the consumer.

As such, Applicants have surprisingly found that whey protein micelles can act as a masking substance for preventing the unpleasant bitterness perception of a specific nutrient by masking a bitter taste receptor present at the surface of the tongue. As presented by the Noriao Ishibashi model, bitterness is an unpleasant gustative sensory perception that often induces food rejection. Sensitivity to bitterness varies from 1 to 500 as a function of each specific person. See, Ishibashi, N. et al., *A Mechanism for Bitter Taste Sensibility in Peptides*, Agr. Biol. Chem. 52, 819-827 (1988).

In addition to whey protein micelles, the skilled artisan will appreciate that the use of micellar casein proteins, as well as any potential vegetable proteins, may also be used as a protein component that masks the bitterness or off-flavor provided to a nutritional composition by leucine or other similar nutrients.

In an embodiment, the whey protein micelles and leucine may be part of a complete nutrition product. As used herein, "complete nutrition" products are preferably nutritional products that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions.

The whey protein micelles and leucine may alternatively be part of an incomplete nutrition product. As used herein, "incomplete nutrition" products are preferably nutritional products that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

Similarly, the whey protein micelles and leucine may be included in tube feed compositions. As used herein, a "tube feed" is preferably a complete or incomplete nutritional products that are administered to an animal's gastrointestinal system, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports.

In an embodiment, the whey protein micelles and leucine may be used in compositions for short term administration. As used herein, "short term administrations" are preferably continuous administrations for less than 6 weeks. Alternatively, the whey protein micelles and leucine may be used in compositions for long term administration. As used herein, "long term administrations" are preferably continuous administrations for more than 6 weeks.

FIG. 1 illustrates a schematic representation of the micelles used in the present disclosure, wherein the whey proteins are arranged in such a way that the hydrophilic parts of the proteins are oriented towards the outer part of the agglomerate and the hydrophobic parts of the proteins are oriented towards the inner "core" of the micelle. The name "whey protein micelle" is indicative of homology with casein micelles based on the following criteria: shape, size, and whitening properties, but also the whey protein micelle is a spherical whey protein micro-gel of denatured whey protein. Both physical and chemical interactions are involved in whey protein microgels or whey protein micelle. In FIG. 1, S* indicates accessible thiol/activated thiol from cysteine, and S—S indicates disulfide bridges stabilizing the whey protein micelle. This energetically favorable configuration offers good stability to these structures in a hydrophilic environment. As such, the micelles consist essentially of spherical agglomerates of denatured whey protein. The micelles are particularly characterised by their regular, spherical shape.

Due to their dual character (hydrophilic and hydrophobic), this denatured state of the protein seems to allow interaction with a hydrophobic phase, e.g., a fat droplet or air, and a hydrophilic phase. The whey protein micelles therefore have perfect emulsifying and foaming properties.

The micelles of the present disclosure may have an extremely sharp size distribution such that more than 80% of the micelles produced will have a size smaller than 1 micron, preferably between 100 nm and 900 nm, more preferably between 100-770 nm, most preferably between 200 and 400 nm. Without wishing to be bound by theory, it is thought that during micelle formation, the micelles reach a "maximum" size, due to the overall electrostatic charge of the micelles repelling any additional protein molecule, such that the micelles cannot grow in size any longer. This accounts for the narrow size distribution presently observed.

As discussed above, the whey protein micelles of the present disclosure may be produced by the methods described in International Application PCT/EP2007/052877, filed Mar. 26, 2007; International Application PCT/EP2007/052900, filed Mar. 27, 2007; and U.S. Ser. No. 12/280,244, filed Aug. 21, 2008, the entire contents of each of which are included herein by reference. An advantage of using the methods described in such applications is that the whey protein micelles prepared accordingly have not been submitted to any mechanical stress leading to reduction of the particle size during formation, contrary to conventional processes known in the art. Instead, the methods induce spontaneous micellization of whey proteins during heat treatment in the absence of shearing. The skilled artisan will appreciate, however, that the micelles may be produced by methods other than those described in the above-mentioned applications.

Any commercially available whey protein isolates or concentrates may be used in accordance with the present disclosure. For example, whey protein obtained by any process for the preparation of whey protein known in the art, as well as whey protein fractions prepared therefrom or proteins such as β-lactoglobulin, α-lactalbumin and serum albumin. In particular, sweet whey obtained as a by-product in cheese manufacture, acid whey obtained as a by-product in acid casein manufacture, native whey obtained by milk microfiltration or rennet whey obtained as a byproduct in rennet casein manufacture may be used as the whey protein. The whey protein may be from a single source or from mixtures of any sources. It is preferable that the whey protein does not undergo any hydrolysis step prior to micelle formation. Thus, the whey protein is not subjected to any enzymatic treatment prior to micellization. According to the present disclosure, however, it is important that the whey protein be used in the micelle formation process and not hydrolysates thereof.

The present disclosure is not restricted to whey isolates from bovine origin, but pertains to whey isolates from all mammalian animal species, such as from sheep, goats, horses, and camels. Also, the process according to the present disclosure applies to mineralised, demineralised or slightly mineralised whey preparations. By "slightly mineralised" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

Whey proteins are an excellent source of essential amino acids (e.g., about 45% by weight). Compared to casein (containing 0.3 g cysteine/100 g protein), for example, sweet whey proteins contain 7 times more cysteine, and acid whey contains 10 times more cysteine. Cysteine is the rate limiting amino acid for glutathione synthesis, a tripeptide made of glutamate cysteine and glycine which has primary important functions in the defence of the body in case of stress. Requirements in these amino acids may be increased in case of stress and in elderly people. Also, glutathione oral supplementation with whey protein has been shown to increase plasma glutathione levels of HIV-infected patients. See, Eur. J. Clin. Invest. 31, 171-178 (2001).

Other health benefits provided by whey proteins include enhancement of muscle development and building, as well as muscle maintenance in children, adults or elderly people, enhancement of the immune function, improvement of cognitive function, control of blood glucose such that they are suitable for diabetics, weight management and satiety, anti-inflammatory effects, wound healing and skin repair, lowering of the blood pressure, etc.

Additionally, whey proteins have a better protein efficiency ratio (PER=118) compared for example to casein (PER=100). PER is a measure of a protein quality assessed by determining how well such protein supports weight gain. It can be calculated by the following formula:

| Examples: | PER | % Casein |
| --- | --- | --- |
| casein | 3.2 | 100 |
| Egg | 3.8 | 118 |
| Whey | 3.8 | 118 |
| Whole Soya | 2.5 | 78 |
| Wheat gluten | 0.3 | 9 |

PER = body weight growth (g)/protein weight intake (g)

To manufacture whey protein micelles according to methods disclosed in the Nestec S.A. patent applications mentioned above, whey proteins may be present in an aqueous solution in an amount of 0.1 wt % to 12.0 wt %, preferably in an amount of 0.1 wt % to 8 wt %, more preferably in an amount of 0.2 wt % to 7.0 wt %, even more preferably in an amount of 0.5 wt % to 6.0 wt %, most preferably in an amount of 1.0 wt % to 4.0 wt % on the basis of the total weight of the solution.

The aqueous solution of the whey protein preparation as present before the micellization step may also comprise additional compounds, such as by-products of the respective whey production processes, other proteins, gums or carbohydrates. The solution may also contain other food ingredients (fat, carbohydrates, plant extracts, etc). The amount of such additional compounds preferably does not exceed 50 wt %, preferably 20 wt %, and more preferably does not exceed 10 wt % of the total weight of the solution.

The whey protein may be used in purified form or likewise in form of a crude product. According to an embodiment, the content of divalent cations in the whey protein for the preparation of the whey protein micelles concentrate may be less than 2.5%, more preferably less than 2%, even more preferably less than 0.2%. In an embodiment, the whey proteins are completely demineralized.

According to the present disclosure, the pH and the ionic strength are important. Thus, for extensively dialyzed samples which are virtually devoid or depleted of free cations such as Ca, K, Na, Mg, it has been found that when performing the heat treatment during a time period of 10 seconds to 2 hours at a pH below 5.4, curd is obtained, while at a pH exceeding 6.8, soluble whey protein results. Thus, only in this rather narrow pH window will whey proteins micelles having a diameter of less than 1 μm be obtained. These micelles will have an overall negative charge. The same micelle form can also be obtained symmetrically below the isoelectrical pH, i.e., from 3.5 to 5.0, more preferably 3.8 to 4.5, resulting in micelles being positively charged.

Thus, according to an embodiment, in order to obtain positively charged micelles, micellization of whey proteins may be done in a salt free solution at a pH value adjusted between 3.8 and 4.5 depending on the mineral content of the protein source.

In an embodiment, the micelles obtained will have an overall negative charge. Thus, in an embodiment, the pH is adjusted to a range of from 6.3 to 9.0, for a content in divalent cations comprised between 0.2% and 2.5% in whey protein powder.

More specifically, to obtain negatively charged micelles, the pH is adjusted to a range of from 5.6 to 6.4, more preferably from 5.8 to 6.0 for a low divalent cation content (e.g., less than 0.2% of the initial whey protein powder). The pH may be increased up to 8.4 depending on the mineral content of whey protein source (concentrate or isolate). In particular, the pH may be between 7.5 to 8.4, preferably 7.6 to 8.0 to obtain negatively charged micelles in the presence of large amounts of free minerals and the pH may be between 6.4 to 7.4, preferably 6.6 to 7.2 to obtain negatively charged micelles in the presence of moderate amounts of free minerals. As a general rule, the higher the calcium and/or magnesium content of the initial whey protein powder, the higher the pH of micellization.

In order to standardize the conditions of formation of the whey protein micelles, it is most preferable to demineralize by any of the known demineralization techniques (dialysis, ultrafiltration, reverse osmosis, ion exchange chromatography, etc.), any source of liquid native whey proteins with a protein concentration ranging from that of sweet whey, microfiltration permeate of milk or acid whey (0.9% protein content) to that of a concentrate at 30% protein content. The dialysis can be done against water (distilled, deionized or soft), but as this will only allow removal of the ions weakly bound to the whey proteins, it is more preferable to dialyze against an acid at pH below 4.0 (organic or inorganic) to better control the ionic composition of the whey proteins. By doing so, the pH of whey protein micelle formation will be below pH 7.0, more preferably comprised between 5.8 to 6.6.

Prior to heating the whey protein aqueous solution, the pH is generally adjusted by the addition of acid, which is preferably food grade, such as e.g., hydrochloric acid, phosphoric acid, acetic acid, citric acid, gluconic acid or lactic acid. When the mineral content is high, the pH is generally adjusted by the addition of alkaline solution, which is preferably food grade, such as sodium hydroxide, potassium hydroxide or ammonium hydroxide.

Alternatively, if no pH adjustment step is desired, it is possible to adjust the ionic strength of the whey protein preparation while keeping the pH constant. Then, ionic strength may be adjusted by organic or inorganic ions in such a way that allows micellization at a constant pH value of 7. In an embodiment, micelles may be formed at a constant pH value of 7.0 while the ionic strength is varied by the addition of 70-80 mM of arginine HCl.

A buffer may be further added to the aqueous solution of whey protein so as to avoid a substantial change of the pH value during heat treatment of the whey protein. In principle, the buffer may be selected from any food-grade buffer system, i.e., acetic acid and its salts, such as, e.g., sodium acetate or potassium acetate, phosphoric acid and salts thereof, e.g., $NaH_2PO_4$, $Na_2HPO_4$, $KH_2PO_4$, $K_2HPO_4$, or citric acid and salts thereof, etc.

Adjusting the pH and/or the ionic strength of the aqueous solution, according to the present disclosure, results in a controlled process yielding micelles having a size between 100 nm-900 nm, preferably between 100 nm-700 nm, most preferably between 200 nm-400 nm. Preferably, the proportion of micelles with an average size comprised between 100-700 nm is greater than 80% when carrying out the process of the disclosure.

In order to obtain regular shape micelles, it is also important that the whey protein does not undergo any hydrolyzation step prior to micelle formation.

In a second step of the process, the starting whey protein aqueous solution is then subjected to the heat treatment. In this respect, it has been found that for obtaining whey protein micelles, it is important to have the temperature in the range of from about 70° C. to below 95° C., preferably from 80° C. to about 90° C., more preferably of from about 82° C. to about 89° C., even more preferably of from about 84° C. to about 87° C., most preferred at about 85° C. It has also been found that, on an industrial scale, it is important that the temperature be preferably less than 95° C., more preferably between 80° C. and 90° C., most preferably about 85° C.

Once the desired temperature has been reached, it is kept at this temperature for a minimum of 10 seconds and a maximum of 2 hours. Preferably, the time period during which the aqueous whey protein solution is kept at the desired temperature ranges from 12 to 25 minutes, more preferably from 12 to 20 minutes, or most preferably about 15 minutes.

The heat treatment may also be achieved in a microwave oven or any similar equipment allowing heating by microwaves with a time/quantity ratio of 10 s/10 mL for a 4 wt % protein solution heated in a 1500 W apparatus up to boiling temperature (98° C. at an altitude of 833 m). A continuous process may also be used by addition of 8 or more magnetrons around a glass tube potentially prolonged by a holding tube to increase the time of incubation.

Turbidity measurements are an indication of micelle formation. According to the present disclosure, the turbidity measured by absorbance at 500 nm is at least 3 absorbance units for 1% protein solution but can reach 16 absorbance units when the yield of micellization is above 80%.

To further illustrate the effect of micelle formation from a physicochemical point of view, a 1 wt % dispersion of Bipro® has been heated for 15 minutes at 85° C. at pH 6.0 and 6.8 in MilliQ water. The hydrodynamic diameter of the aggregates obtained after heat treatment was measured by dynamic light scattering. The apparent molecular weight of the aggregates was determined by static light scattering using the so-called Debye plot. The surface hydrophobicity was probed using the hydrophobic ANS probe and the free accessible thiol groups by the DTNB method using cystein as the standard amino acid. Finally, the morphology of the aggregates was studied by negative staining TEM. The results are presented in Table 1.

TABLE 1

Physicochemical properties of whey protein aggregates obtained by heat treatment (85° C., 15 min) of a 1 wt % protein dispersion at pH 6.0 or 6.8.

| pH | hydrodynamic diameter (nm) | molecular weight $M_w$ ($\times 10^6$ g·mol$^{-1}$) | morphology | ζ-potential (mV) | protein surface hydrophobicity (μg·mmol$^{-1}$ ANS) | accessible SH groups (nmol SH·mg$^{-1}$ prot.) |
|---|---|---|---|---|---|---|
| 6.0 | 120.3 ± 9.1 | 27.02 ± 8.09 | Spherical micelles | −31.8 ± 0.8 | 105.4 | 3.5 ± 0.4 |
| 6.8 | 56.2 ± 4.6 | 0.64 ± 0.01 | linear aggregates | −27.9 ± 1.2 | 200.8 | 6.8 ± 0.5 |

From Table 1, it is clear that the whey protein micelles that were formed at pH 6.0 allow protein to decrease its specific ANS surface hydrophobicity by a factor of 2 compared to non-micellized whey protein heated in the same condition, but at pH 6.8. The micelle formation can be also seen on the very high molecular weight of 27×10$^6$ g·mol$^{-1}$ compared to 0.64×10$^6$ g·mol$^{-1}$ for non-micellized protein, indicating a very condensed state of the matter within the micelle (low amount of water). Interestingly enough, the ζ-potential of the micelles is even more negative than the non-micellized proteins even if the latter have been formed at a more basic pH than the micelles. This is the result of a more hydrophilic surface of the micelles being exposed to the solvent. Finally, one should note that the thiol reactivity of the micelles is much lower than that of the non-micellized protein because of the different pH of heat treatment.

It has been found that the conversion yield of native whey protein to micelles decreases when the initial protein concentration is increased before pH adjustment and heat treatment. For example, when starting with a whey protein isolate PROLACTA® 90 (lot 673 from Lactalis), the yield of formation of whey protein micelles drops from 85% (when starting with 4% proteins) to 50% (when starting with 12% of proteins). In order to maximize the formation of whey protein micelles (>85% of the initial protein content), it is better to start with an aqueous whey protein solution having a protein concentration below 12%, preferably below 6%. Depending on the intended final applications, the protein concentration is adjusted before heat treatment to manage the optimal whey protein micelles yield.

The whey proteins micelles obtained according to the methods of the Nestec S.A. patent applications mentioned above shall have an average size of less than 1 μm, preferably of from 100 nm to 900 nm, more preferably from 100 nm to 700 nm, most preferably from 200 nm to 400 nm.

Depending on the desired application, the yield of micelles before concentration is at least 35%, preferably at least 50%, more preferably at least 80% and the residual soluble aggregates or soluble protein content is preferably below 20%. The average micelle size is characterized by a polydispersity index below 0.200. It has been observed that whey protein micelles could form aggregates around pH 4.5, with however no sign of macroscopic phase separation after at least 12 hours at 4° C.

The purity of whey protein micelles produced according to the methods of the Nestec S.A. patent applications mentioned above can be obtained by determining the amount of residual soluble proteins. Micelles are eliminated by centrifugation at 20° C. and 26900 g for 15 min. The supernatant is used to determine the protein amount in quartz cuvettes at 280 nm (1 cm light pathlength). Values are expressed as a percentage of the initial value before heat treatment.

Proportion of micelles=(Amount of initial proteins−amount of soluble proteins)/Amount of initial proteins An advantage of the methods described herein is that the whey protein micelles prepared accordingly have not been submitted to any mechanical stress leading to reduction of the particle size during formation, contrary to conventional processes. This method induces spontaneous micellization of whey proteins during heat treatment in the absence of shearing.

The whey protein micelles may be used as such in any composition, such as nutritional compositions, cosmetic compositions, pharmaceutical compositions, etc. According to the present disclosure, the whey protein micelles are used in consumable products. Furthermore, the whey protein micelles may be filled with an active component. Said component may be selected from coffee, caffeine, green tea extracts, plant extracts, vitamins, minerals, bioactive agents, salt, sugar, sweeteners, aroma, fatty acids, oils, protein hydrolysates, peptides, amino acids, etc., or combinations thereof.

Further, the whey protein micelles (pure or filled with active components) of the present disclosure may be coated with an emulsifier such as phospholipids, for example, or other coating agents such as a protein, a peptide, a protein hydrolysate or a gum such as acacia gum in order to modulate the functionality and the taste of the whey protein micelles. When a protein is used as a coating agent, it may be selected from any proteins having an isoelectric point significantly higher or lower than whey protein. These are, for example, protamine, lactoferrin and some rice proteins. When a protein hydrolysate is used as coating agent, it is preferably a hydrolysate from proteins such as protamine, lactoferrin, rice, casein, whey, wheat, soy protein, or combinations thereof. In an embodiment, the coating is an emulsifier selected from sulfated butyl oleate, diacetyltartaric acid esters of mono- and diglycerides, citric acid esters of monoglycerides, stearoyl lactylates, or combinations thereof. In an embodiment, the coating is sulfated butyl oleate. Coating may be carried out by any methods known in the art. Furthermore, co-spray-drying, as described further herein, may also result in a coating of the whey protein micelles.

The whey protein micelles have shown to be ideally suited for use as an emulsifier, fat substitute, substitute for micellar casein or foaming agent, since they are able to stabilize fat and/or air in an aqueous system for prolonged period. Indeed, whey protein micelles may be used as an emulsifying agent, for which the material is ideally suited, since it has a neutral taste and no off-flavor is created by the use of such material. They may also be used as micellar casein substitute.

In addition, the present whey protein micelles may serve as whitening agent, so that with one compound several tasks may be fulfilled. Since whey is a material abundantly available, the use thereof reduces the cost of a product requiring an emulsifying, filling, whitening or foaming agent, while at the same time adding to its nutritional value.

Accordingly, the whey protein micelles obtainable by the methods described herein can be used for the preparation of any kind of consumable product requiring stabilization of an emulsion or a foam, such as e.g., present in mousse or ice cream, in coffee creamers, or also in low fat or essentially fat free dairy products, or also where it finds application as a micellar casein substitute.

By "consumable" is meant any food product in any form, including beverages, soups, semi-solid foods, etc., which can be consumed by a human or an animal. Examples of products, where the present whey protein micelles may find application are for example, dairy products, mayonnaise, salad dressing, pasteurized UHT milk, sweet condensed milk, yoghurt, fermented milks, sauces, reduced fat sauces such as bechamel-type sauce for instance, milk-based fermented products, milk chocolate, white chocolate, dark chocolate, mousses, foams, emulsions, ice creams, fermented cereal based products, milk based powders, infant formula, diet fortifications, pet food, tablets, liquid bacterial suspensions, dried oral supplement, wet oral supplement, performance nutrition bars, spreads, fruit drinks, coffee mixes, etc.

The nutritional compositions and products of the present disclosure may be either powder or liquid compositions. When the compositions are liquid, whey protein micelles and other powder ingredients such as, for example, active ingredients, functional ingredients, leucine, etc., may be added to a reconstitution liquid to form a liquid nutritional composition or product. The reconstitution liquid may be any consumable liquid including, but not limited to, water, deionized water, carbonated water, fruit juice, milk, syrups, and other water-based beverages such as tea. In an embodiment, the powder whey protein micelles and leucine may also be added to foods such as eggs to form an emulsion. The skilled artisan will appreciate that any type of food and/or liquid may be used as a base or carrier for the whey protein micelles and leucine.

Thus, a consumable product comprising whey protein micelles is part of the present disclosure, as is discussed above. By "whey protein micelles" are meant spherical agglomerates of denatured whey protein. Preferably, the whey protein is not hydrolyzed prior to micelle formation, such that regular shape, spherical micelles are obtained. In the micelles, the whey protein are arranged in such a way that the hydrophilic parts of the proteins are oriented towards the outer part of the agglomerate and the hydrophobic parts of the protein are oriented towards the inner core of said micelle. Typically, the whey protein micelles have a size of less than 1 micron.

According to an embodiment, and as discussed above, the consumable product comprises whey protein micelles and an additional nutrient such as, for example, an amino acid. Non-limiting examples of amino acids include Isoleucine, Alanine, Leucine, Asparagine, Lysine, Aspartate, Methionine, Cysteine, Phenylalanine, Glutamate, Threonine, Glutamine, Tryptophan, Citrulline, Glycine, Valine, Proline, Serine, Tyrosine, Arginine, Histidine, or combinations thereof.

In an embodiment, the consumable product comprises whey protein micelles and leucine in an amount sufficient to stimulate protein synthesis in humans while avoiding an increase in viscosity due to the whey protein or poor organoleptic properties due to the high amounts of leucine present in the composition. Generally, the quantity of leucine present in the nutritional compositions or products will depend on the final volume of the compositions or products, as well as the fact that the limit of leucine solubility at 25° C. is 2.426 g per 100 g liquid, and the fact that 10 g of whey protein micelles inherently includes about 1 g of leucine. Based on this information, it is possible to achieve a high amount of leucine in a nutritional composition without experiencing poor organoleptic properties.

For example, a dry weight ratio of added leucine to whey protein micelles in the present compositions may be from about 1:2 to about 1:3. In an embodiment, the dry weight ratio of added leucine to whey protein micelles is about 1:2.6. Alternatively, a liter of a nutritional composition may contain up to about 25 g of total leucine. In an embodiment, a liter of a nutritional composition may contain about 24 g of leucine. In another example, 100 g of a liquid may contain up to about 2.5 g of leucine. In an embodiment, 100 g of a liquid may contain about 1 to about 2 g of leucine, or about 1 g to about 3 g of leucine, or about 2.462 g of leucine. In an example where the composition is a powder composition, the composition may include a total dry matter weight percent of leucine between about 20% and about 40%. In an embodiment, the total dry matter weight percent of leucine in a powder composition is about 37%. Additionally, the total dry weight of added leucine may be about 30% to about 40% of the total dry weight of the whey protein micelles. In an embodiment, the total dry weight of added leucine may be about 37% of the total dry weight of the whey protein micelles. The skilled artisan will be able to adjust these amounts of leucine based on the serving size of the nutritional composition or product.

For example, the nutritional compositions and products may also be provided in a variety of serving sizes as long as the amounts of whey protein micelles and leucine are scaled accordingly. For example, and as discussed above, the limit of leucine solubility at 25° C. is about 2.426 g per 100 g liquid. Using this information, a serving size of 250 ml, which may contain from about 3 to 6 g leucine by amount dry weight or have a leucine to whey protein micelle ratio of about 1 to 2.6, may be changed to increase or decrease the amount of composition or product provided to a patient. For example, the serving size may also be a shot (e.g., 80-100 ml), a can (e.g., 120 or 250 or 375 ml), a pouch (e.g., 1 liter or 1.5 to 2 liters), or a powder in a module to supplement conventional diet or enteral products.

In a specific example, a 250 ml serving size of a nutritional composition may include, by weight dry matter, 10.1 g of whey protein micelles, 3.8 g of added leucine, and 55.6 g of other ingredients to create a dry matter composition of about 69.5 g. In this example, the total amount of leucine in the product is about 4.8 g (1 g from the whey protein micelles and 3.8 g of added leucine), and the whey protein micelles are about 14.5% of the total dry volume and the added leucine is about 5.5% of the total dry volume. The total dry weight percentage of leucine in this example would be 6.9% (4.8 g of total leucine/69.5 g of total dry matter).

As discussed above, whey protein micelles may be used in nutritional compositions to mask off-flavors of nutrients to mask tongue bitter taste receptors. Indeed, it is believed that the structure of the protein micelles and their interaction with leucine (or other off-flavor nutrients) prevent the unpleasant bitterness perception by a consumer. Accordingly, in addition to compositions containing whey protein micelles, the present disclosure also includes methods of making and using such compositions.

Figure 2:
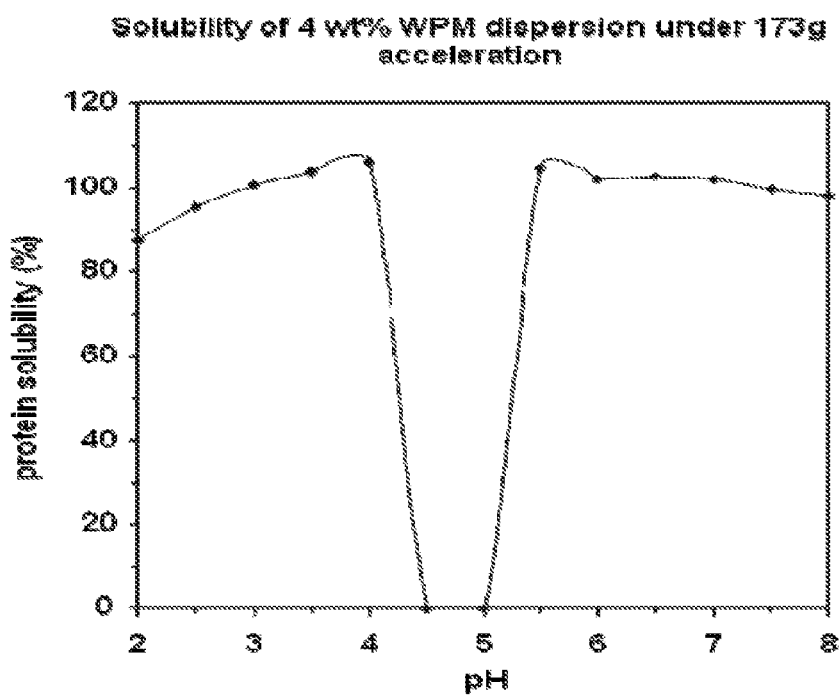
FIG. 2 shows a solubility curve of whey protein micelles at different pH in accordance with an embodiment of the present disclosure.

According to another embodiment, the consumable product comprises whey protein micelles which are soluble in the product and has a pH below 4. A solubility curve for whey protein micelles is provided at FIG. 2. As shown by FIG. 2, whey protein micelles are more soluble and stable below pH 4.0 and above pH 5.5. In addition, whey protein micelles could be used in the critical solubility region, pH 4.5 to pH 5.0, for gels or malleable protein texture. By "soluble" it is meant that the micelles do not aggregate or coagulate to form insoluble aggregates of whey protein micelles. In other words, the whey protein micelles are dispersed in the product. This presents the advantage that acidic products may comprise the whey protein micelles according to the disclosure without any problems of stability.

Similarly, products having a salt content above 0.01%, even above 0.1%, even above 1% and comprising soluble whey protein micelles are also part of the disclosure. The whey protein micelle stability in salty or acidic food matrices is of considerable advantage.

For instance, consumable products such as a mayonnaise, a low-fat or non-fat mayonnaise, a sauce such as a bechamel-type sauce, a Hollandaise-type sauce, tartar sauce, pasta sauce, a white sauce, a pepper sauce, sauce with pieces, sauce for oven dishes such as salmon cream gratin, a soup, a creamy soup such as champignon cream soup, asparagus cream soup, broccoli cream soup, a That soup, a vegetable soup, a salad cream, a dressing, a custard, spreads, dips, salads, etc., which comprise whey protein micelles may be produced. The presence of whey protein micelles confers to the products all the advantages described in the present application, such as protein enrichment, whitening/opacifying effect, fat reduction, enhanced creamy texture and mouthfeel, etc.

An acidic mayonnaise-type product comprising soluble whey protein micelles is a product according to the disclosure. By mayonnaise-type product is to be understood any condiment sauce having the texture and appearance of mayonnaise. It may be a standard mayonnaise, a salad mayonnaise, a salad cream, a dressing, a spread, a dip, etc. Typically, the pH of the mayonnaise-type product of the disclosure is between 2 and 6, preferably between 2.5 and 4.5. The product may also comprise salt in an amount of 0-3%, preferably between 0.1 and 2.5%, most preferably between 0.1 and 1.5%. The product may comprise less than 50% fat, 50-70% fat or above 70% fat. Preferably, the product comprises no fat. The product may or may not be based on an emulsion.

Other ingredients present in the mayonnaise-type product of the disclosure, may include egg products (e.g., egg yolk, white of chicken egg, product based on chicken egg etc.), sugars, condiment, spices, aromatic herbs, fruit and vegetables including fruit and vegetable juices, mustard, milk products, water, emulsifiers, thickeners, etc.

According to another embodiment, a soup or sauce product comprising soluble whey protein micelles and having a salt content between 0.01-3%, preferably 0.1-2.5% is also provided. The soup or sauce product may also be acidic, for example in tomato soups or sauces, etc. Typically, the soup or sauce product is savory although it may, in some cases, be sweet (e.g., Polish soups). Typically, the soup or sauce product of the disclosure comprises a flavor base and thickening agents. The flavor base may comprise salt, flavorings, flavor enhancers, spices, etc., or combinations thereof. The thickening agents may be selected from starches, gums, flours, etc., or combinations thereof. Furthermore, the soup or sauce product may comprise other ingredients selected from fat, cream, creamer, oil, emulsifiers, vegetables, legumes, garnishes, pasta, meat, dumplings, milk products, or combinations thereof. Preferably, the soup or sauce product is non-fat or fat reduced. Examples of such sauce products are Bechamel-type sauce, Hollandaise-type sauce, white sauce, pasta sauce, sauce with pieces, sauce for oven dish such as salmon cream gratin, pepper sauce, tartar sauce, etc. Soup products may include creamy soup such as asparagus, broccoli, champignon cream soups, That soups, vegetable soups, etc.

The products described above may be provided as "ready-to-eat" products, i.e., they may be consumed as such without addition of further ingredients such as water, for example. Alternatively, they may be reconstituted products from a dehydrated mix.

The products described herein may be produced by mixing whey protein micelles, a concentrate thereof or a powder thereof with further ingredients and processing the mixture. The processing may involve any processing step used in the manufacture of food product known in the art. These may be subjecting the mixture to heat, pressure, acid or basic conditions, cold, etc.

In another aspect, the disclosure also provides for dehydrated products such as instant soups, sauces, condiments, cook-up soups, etc., which can be easily reconstituted with water or other liquid to make them suitable for consumption.

Typically, the dehydrated product of the disclosure comprise whey protein micelle powder and dried food ingredients. The whey protein micelle powder is described in the present application. It may consist of spray-dried whey protein micelles. Alternatively, the whey protein micelle powder comprises additional ingredients which may be selected from soluble or non-soluble salts, probiotic bacteria, stains, sugars, maltodextrins, fats, oils, fatty acids, emulsifiers, sweeteners, aroma, plant extracts, ligands, bioactive agents, caffeine, vitamins, minerals, drugs, milk, milk protein, skimmed milk powder, micellar casein, caseinate, vegetal protein, protein hydrolysates such as wheat gluten hydrolysate, peptides, amino acids, polyphenols, pigments, yeast extracts, monosodium glutamate, etc., or combinations thereof.

When the whey protein micelle powder comprises further ingredients, the ratio of whey protein micelle to additional ingredient is preferably 1:1 to 1:100.

The dried food ingredients present in the dehydrated products of the disclosure are selected from carbohydrates, protein sources, starches, fibers, fat, flavorings, spices, salts, etc., or combinations thereof.

The ratio of whey protein micelle powder to further dried ingredients is typically in the range of 1:1 to 1:10, preferably 1:1 to 1:5, most preferably 1:3.

Such dehydrated product may be manufacture by mixing a whey protein micelle powder with further dried ingredients or co-drying a whey protein micelle solution or concentrate with further ingredients. Typically, this is achieved by co-spray-drying. Furthermore, the present whey protein micelles may be used either alone or together with other active materials, such as polysaccharides (e.g., acacia gum or carrageenans) to stabilize matrices and for example milky foam matrices. Due to their neutral taste, their whitening power and their stability after heat treatment, the present whey proteins micelles may be used to increase skimmed milk whiteness and mouth feel.

As well as increasing the whitening power of dairy systems for the same total protein content, the fat content in a food matrix may be reduced. This feature represents a particular advantage of the present whey protein micelles, since it allows producing low-fat products, for example adding a milk creamer without adding additional fat derived from the milk as such.

In an embodiment, the whey protein micelle dispersion obtained after heat treatment is concentrated to yield a whey protein micelle concentrate. The concentration step may be carried out by evaporation, centrifugation, sedimentation, ultrafiltration and/or by microfiltration. Evaporation may be carried out on the micelles dispersion by feeding it to an evaporator under vacuum, having a temperature between 50° C. and 85° C. Centrifugation may be carried out with high acceleration rate (more than 2000 g) or low acceleration rate (less than 500 g) after acidification of the whey protein micelle dispersion at a pH lower than 5, preferably 4.5. Spontaneous sedimentation may also be carried out on the whey protein micelle dispersion by acidification. Preferably, the pH will be 4.5 and the sedimentation time is more than 12 hours.

In an embodiment, concentration of the whey protein micelles may be achieved by microfiltration of the micelles dispersion. This enriching technique not only enables to concentrate whey protein micelles by removing the solvent but also enables the removal of non-micellized protein (such as native proteins or soluble aggregates). Thus, the final product only consists of micelles, as was verified by Transmission Electron Microscopy. In this case, the concentration factor that is possible to achieve is obtained after the initial flow rate of permeate through the membrane has dropped to 20% of its initial value.

The whey protein concentrate will have a protein concentration of at least 12%. Furthermore, the concentrate will contain at least 50% of the protein in the form of micelles.

It is interesting to note that the concentrate, if adjusted to a protein content of 10% has the ability to withstand a subsequent heat treatment at 85° C. for 15 min at pH 7.0 in presence for example of up to 0.15 M of sodium chloride. As a matter of comparison, a native whey protein dispersion (PROLACTA® 90, lot 500658 from Lactalis) forms a gel in the presence of 0.1 M of sodium chloride at a protein concentration of only 4%.

The micelles used in the present disclosure also present the benefit that the high stability of the micelle structure is preserved during the concentration step. Furthermore, the micelles according to the present disclosure have a Protein Efficiency Ratio (PER) equivalent to the starting whey protein of at least 100, preferably at least 110, which makes them important nutritional ingredients.

The enrichment of the whey protein micelles offers the exceptional advantages that protein-enriched products may be obtained at concentration previously not attainable. Furthermore, since the concentrate may act as a fat substitute while maintaining desirable structural, textural and organoleptic properties, a wider variety of low-fat product may be obtained.

Additionally, it presents the cost advantage that a smaller amount of concentrate is needed to obtain the desired effects.

The whey protein micelle concentrate (from evaporation or microfiltration) can be used in liquid form as a dispersion or in semi-solid form, or in a dried form. It may be used in a great variety of applications such as those described above with respect to the whey protein micelles applications. For instance, the 20% protein concentrate obtained by evaporation has a creamy, semi-solid texture and can be texturized in a spreadable texture by acidification using lactic acid. This liquid, creamy, pasty texture can be used to prepare acid, sweet, salty, aromatic, protein-rich consumables.

The whey protein micelles concentrate in any form may be mixed with 5% of an acidic fruit base and 5% of sucrose in order to obtain a stable whey protein enriched acidic fruit drink. It may also be used in the manufacture of milk products, ice cream, or used as coffee whitener amongst others.

Further applications include skin care and mouth care, such as toothpaste, chewing gum, or gum-cleaning agent for instance.

The whitening power of the concentrate in any form is tremendously increased in comparison to the non-concentrated micelles or to the native protein powders. For example, the whitening power of 4 mL of a 15% whey protein micelle concentrate is equivalent to 0.3% of titanium oxide in 100 mL of a 2% soluble coffee cup. Interestingly, it is possible to disperse soluble coffee and sucrose into a whey protein micelle concentrate so that a 3-in-1 concentrate having a total solids concentration of 60% without fat is obtained.

The concentrate may be used as such or diluted depending on the application. For instance, the whey protein micelle concentrate in liquid or dried form may be diluted to a protein content of 9% like in sweet and condensed milk. The milk minerals, lactose and sucrose can be added so that the final product will have similar nutritional profile compared to milk, but only whey protein as the protein source. This whey protein based blend is more stable than sweet condensed milk against Maillard reaction (based on the speed of development of a brown color) when incubated 2 hours at 98° C. (temperature of boiling water at an altitude of 833 m).

The dried form of the whey protein concentrate obtainable by the method described herein may be obtained by any known techniques, such as spray-drying, freeze-drying, roller drying, etc. Thus, the whey protein concentrate of the present disclosure may be spray-dried with or without addition of further ingredients and may be used as a delivery system or a building block to be used in a wide range of processes, e.g., consumables production, cosmetic applications, etc.

In an embodiment, a powder is obtained by spray-drying without addition of any further ingredients, and has an average particle diameter size greater than 1 micron due to the micelle aggregation occurring during spray-drying. A typical average volume median diameter (D43) of the powders of the disclosure is between 45 and 55 microns, preferably 51 microns. The surface median diameter (D32) of the powders of the present disclosure is preferably between 3 and 4 microns, more preferably it is 3.8 microns. The moisture content of the powders obtained after spray-drying is preferably less than 10%, more preferably less than 4%.

Such a whey protein micelle powder may comprise at least 90% whey protein, from which at least 20%, preferably more than 50%, most preferably more than 80% are in the micellar form.

Furthermore, the whey protein micelles powder used in the present disclosure have a high binding capacity for solvents such as water, glycerol, ethanol, oil, organic solvents, etc. The binding capacity of the powders to water is at least 50%, preferably at least 90%, most preferably about 100%. For solvents such as glycerol and ethanol, the binding capacity is of at least 50%. For oil, the binding capacity is at least 30%. This property of the whey protein micelle powders of the present disclosure allows these to be sprayed or filled with further functional ingredients such as coffee, caffeine, green tea extracts, plant extracts, vitamins, minerals, bioactive agents, salt, sugar, sweeteners, aroma, fatty acids, oils, protein hydrolysates, peptides, amino acids, etc., or combinations thereof.

The functional ingredients may be included in the powder in an amount of 0.1-50%. Thus, the powder may act as a carrier for those functional ingredients. This presents the advantage that, for instance, caffeine bitterness perception is reduced when filled into the powders of the present disclosure and used in caffeinated nutrition bars for instance. Additional ingredients may be mixed to the whey protein micelle concentrate prior to spray-drying. These comprise soluble or non-soluble salts, peptides, protein hydrolysates (e.g., wheat gluten hydrolysate), probiotic bacteria, stains, sugars, maltodextrins, fats, emulsifiers, sweeteners, aroma, plant extracts, ligands, bioactive agents, caffeine, vitamins, minerals, drugs, milk, milk proteins, skimmed milk powder, micellar casein, caseinate, vegetal protein, amino acids, polyphenols, pigment, etc., and combinations thereof. The resulting mixed whey protein micelle powders comprise whey protein micelles and at least one additional ingredient in a weight ratio ranging from 1:1 to 1:100.

This co-spray-drying results in powders consisting of whey protein micelles agglomerated or coated with an additional ingredient. Preferably, the weight ratio of whey protein micelles to additional ingredient is 1:1. This may further facilitate solubilization of these powders and may be of particular interest in the manufacture of dehydrated food products such as soups, sauces, etc., comprising whey protein micelles.

The whey protein micelle powders used in the present disclosure are characterized by an internal structure composed mainly of hollow spheres but also of collapsed spheres. The hollow spheres structure can be easily explained by the formation of the vapor droplet within the WPM concentrate droplet during the spray drying. As the vapor droplet left the WPM droplet due to a temperature above 100° C., a hollow sphere remained. The "bone-shape" is due to a combination of the water evaporation from droplet and the external pressure within the droplet.

The internal structure of the spherical hollow spheres was investigated by SEM after sectioning the particle close to its diameter. The wall thickness of the particle was around 5 μm and seemed very smooth, whereas the inner structure had a more grainy appearance. Increased magnification showed that this graininess was in fact due to the presence of the initial WPM that were fused to form the inner matrix of the powder particle. Interestingly, the spherical shape of the micelles was kept during spray drying as well the homogeneous particle size distribution.

Thus, on a microscopic basis, whey protein micelle powders are characterized by a unique granule morphology of hollow or collapsed spheres containing intact and individualized whey protein micelles.

Whey protein micelle powders are characterized by a very high flowability, which offers advantages not previously obtainable. For instance, these powders behave almost as liquids and present the advantages of easy usability and transferability. The angle of repose of these powders is preferably below 35°, more preferably below 30°. Such a low angle of repose allows the powders of the present disclosure to be used as flowing agents in food applications, for instance.

A very important feature of these powders, mixed or "pure" is that the basic micelle structure of the whey proteins is conserved. Furthermore, the micelle structure can be easily reconstituted in solvents. It has been shown that the powders obtained from whey protein micelle concentrate can be easily redispersed in water at room temperature or at 50° C. The size and structure of the whey protein micelles are fully conserved compared to the initial concentrate. For example, in an embodiment, the whey protein concentrate that was spray-dried at 20% protein concentration has been redispersed in deionised water at 50° C. at a protein concentration of 4%. The structure of the micelles was probed by TEM. The diameter of the micelles was found to be 315 nm by dynamic light scattering with a polydispersity index of 0.2.

The fact that the whey protein micelles and only a minor aggregated fraction were observed in solution after reconstitution and homogenization at 250 bars of the spray-dried or freeze-dried powder confirms that whey protein micelles are physically stable regarding spray-drying and freeze-drying.

The powders of the present disclosure may be used in a wide range of applications, such as all those described above in relation to whey protein micelles and the concentrates thereof. For instance, protein-enriched consumables, such as chocolate, performance nutrition bars, dehydrated culinary products, chewing-gum, etc., can be easily produced by using the micelle concentrate powders. Due to their high stability to processing, the powders of the present disclosure may also be further coated by emulsifiers, gums, proteins, peptides, protein hydrolysates, for instance. This may be advantageous to modulate the functionality and the taste of these powders.

The disclosure is further defined by reference to the following examples describing in detail the preparation of the micelles used in the present disclosure. The disclosure described and claimed herein is not to be limited in scope by the specific embodiments herein disclosed, since these embodiments are intended as illustrations of several aspects of the disclosure. Any equivalent embodiments are intended to be within the scope of this disclosure. Indeed, various modifications of the disclosure in addition to those shown and described herein will become apparent to those skilled in the art from the foregoing description. Such modifications are also intended to fall within the scope of the appended claims.

Example 1

Micellization of β-Lactoglobulin by pH Adjustment

β-Lactoglobulin (lot JE002-8-922, Dec. 13, 2000) was obtained from Davisco (Le Sueur, Minn., USA). The protein was purified from sweet whey by ultra-filtration and ion exchange chromatography. The composition of the powder is 89.7% protein, 8.85% moisture, 1.36% ash (0.079% $Ca^{2+}$, 0.013% $Mg^{2+}$, 0.097% $K^+$, 0.576% $Na^+$, 0.050% $Cl^-$). All other reagents used were of analytical grade (Merck Darmstadt, Germany).

The protein solution was prepared at 0.2% concentration by solvation of β-lactoglobulin in MilliQ® water (Millipore), and stirring at 20° C. for 2 h. Then pH of aliquots was adjusted to 5.0, 5.2, 5.4, 5.6, 5.8, 6.0, 6.2, 6.4, 6.6, 6.8, 7.0 by HCl addition. The solutions were filled in 20 ml glass vials (Agilent Technologies) and sealed with aluminum capsules containing a silicon/PTFE sealing. The solutions were heated at 85° C. for 15 min (time to reach the temperature 2.30-3.00 min). After the heat treatment, the samples were cooled in ice water to 20° C. The visual aspect of products indicates that the optimal pH of micellization is 5.8.

Example 2

Micellization of Whey Protein Isolate

Whey protein isolate (WPI) (Bipro®, Batch JE032-1-420) was obtained from Davisco (Le Sueur, Minn., USA). The composition of the powder is reported in Table 2.

The protein solution was prepared at 3.4% protein by solvation of whey protein powder in MilliQ® water (Millipore), and stirring at 20° C. for 2 h. The initial pH was 7.2. Then pH of aliquots was adjusted at 5.6, 5.8, 6.0, 6.2, 6.4 and 6.6 by HCl 0.1 N addition.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min). After the heat treatment, samples were cooled in ice water to 20° C.

The turbidity of heated whey proteins has been determined at 500 nm and 25° C., samples were diluted to allow the measurement in the range of 0.1-3 Abs unit (Spectrophotometer Uvikon 810, Kontron Instrument). Values were calculated for the initial protein concentration 3.4%.

The pH of micellization was considered to be reached upon stability (less than 5% variation of the initial value) of the absorbance measured at 500 nm within an interval of 10 minutes for the same sample. For this product the optimal pH for micellization was 6.0 to 6.2. For this pH adjusted before heat treatment stable turbidity was 21 and residual soluble protein evaluated by absorbance at 280 nm after centrifugation was 1.9%. We can conclude that 45% of initial proteins were transformed in micelles at pH 6.0.

TABLE 2

Composition of WPI and Sample characteristics after micellisation

| | |
|---|---|
| Supplier | Davisco |
| Product name | BIPRO ® |
| Batch number | JE 032-1-420 |
| Composition (mg/100 g) | |
| Sodium | 650 |
| Potassium | 44 |
| Chloride*10 if ≤40 | 10 |
| Calcium | 82 |
| Phosphorus | 49 |
| Magnesium | 6 |
| Initial pH | 7.2 |
| pH micellisation | 6.0 |
| Turbidity (500 nm) for 3.4% protein in solution | 21 |
| Residual Soluble protein (%) by absorbance at 280 nm | 1.9 |

Example 3

Microscopic Observation of Micelles

Production of Micelles:

Protein solution was prepared at 2% protein by solvation of whey protein powder (WPI 90 batch 989/2, Lactalis, Retier, France) in MilliQ® water (Millipore), and stirred at 20° C. for 2 h. Then pHs of aliquots were adjusted using HCl 0.1N or NaOH 0.1N.

The solutions were filled in 20 ml glass vials (Agilent Technologies) and sealed with aluminum capsules containing a silicon/PTFE sealing. The solutions were heated at 85° C. for 15 min (time to reach the temperature 2.30-2.50 min).

After the heat treatment, the samples were cooled in ice water to 20° C. For this product the optimal pH for micellization was 7.4.

Microscopic Observations:

Liquid micelle samples were encapsulated in agar gel tubes. Fixation was achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples were embedded in Spurr resin (Spurr/ethanol 1:1, 2:1, 100%). After polymerization of the resin (70° C., 48 hours), semi-thin and ultra-thin sections were cut with a Leica ultracut UCT ultra-microtome. Ultra-thin sections, stained with aqueous uranyl-acetate and lead citrate, were examined in transmission electron microscopy (Philips CM12, 80 kV).

Obtained micelles are presenting a spherical shape with a diameter of 200 nm, as measured by TEM.

Particle Size Distribution

The intensity-based size distributions of micelles were measured for those micelles obtained by heat-treatment of a 1 wt % β-lactoglobulin dispersion for 15 min at 85° C. at pH 4.25 (positively charged with a zeta potential around +25 mV) and at pH 6.0 (negatively charged with a zeta potential around −30 mV). Z-averaged hydrodynamic diameter of the micelles was 229.3 mm at pH 4.25 an 227.2 at pH 6.0. β-LG and whey protein aggregations were followed using dynamic light scattering. A Nanosizer ZS apparatus (Malvern Instruments, UK) equipped with a laser emitting at 633 nm and with 4.0 mW power was used. The instrument was used in the backscattering configuration, where detection is done at a scattering angle of 173° C. This allows considerable reduction of the multiple scattering signals found in turbid samples. Samples were placed in a squared quartz cell (Helima, pathlength 1 cm). The path length of the light beam was automatically set by the apparatus, depending on the sample turbidity (attenuation). The autocorrelation function was calculated from the fluctuation of the scattered intensity. The results indicate that the average particle is characterized by a very narrow polydispersity index (<0.200).

Example 4

Micellization of a β-lactoglobulin at a Constant pH

The method described in Example 1 was repeated using an aqueous solution of 2% β-lactoglobulin. The pH of this solution has been adjusted to 7.0 after adding Arginine HCl solutions to obtain a final salt concentration ranging from 5 to 200 mM and a final β-lactoglobulin concentration of 1%. Subsequent heat treatment (80° C., 10 min, about 2 min heating up) was carried out to produce micelles.

The results indicate that only in the ionic strength range of from about 50 to 70 mM, a substantial turbidity can be observed, indicating the presence of whey protein micelles.

Example 5

Preparing a Whitening Agent

Native whey proteins (WPI 95 batch 848, Lactalis; 8 wt % aqueous solution) were treated according to Example 2. The resulting product lightness (L) was measured in trans-reflectance mode using a MacBeth CE-XTH D65 10° SCE apparatus equipped with a 2 mm measuring cell. The resulting lightness was L=74.8, that could be compared to the value of L=74.5 for full-fat milk.

Example 6

Preparing a Coffee Creamer

Native whey proteins (Bipro®, lot JE 032-1-420, 0.5 wt % aqueous solution) were mixed at 50° C. with 10 wt % partially hydrogenated palm oil, 14 wt % maltodextrin (DE 21) and in presence of 50 mM phosphate-citrate buffer adjusted to the micellization pH of 6.0 for this Bipro®. The mixture was homogenized under 400/50 bars using a Rannie homogeniser and subsequently heat-treated for 15 minutes at 85° C.

The emulsion obtained showed a high stability over a time period of at least one month at the conditions of storage at 4° C. and gave a whiteness of L=78 compared to a reference liquid creamer (Creme a Cafe, Emmi, Switzerland) having a fat content of 15% and a lightness of L=75.9.

Example 7

Preparing an Aqueous Foam

Native β-lactoglobulin (Biopure, Davisco, lot JE 002-8-922, 2 wt % aqueous solution) was mixed with 120 mM Arginine HCl solution so that the final β-lactoglobulin concentration was 1 wt % and Arginine HCl 60 mM. The pH was then adjusted to 7.0 by addition of 1N HCl. The mixture was then heat treated at 80° C. for 10 minutes so that 90% of initial β-lactoglobulin was converted into micelles having a z-averaged diameter of 130 nm. In this case, the diameter of the micelles was determined using a Nanosizer ZS apparatus (Malvern Instruments, UK). The sample was poured in a quartz cuvette and variations of the scattered light were recorded automatically. The obtained autocorrelation function was fitted using the cumulants method so that the diffusion coefficient of the particles could be calculated and thereafter the z-averaged hydrodynamic diameter using the Stokes-Einstein law. For this measurement, the refractive index of the solvent was taken as 1.33 and that of the micelles 1.45. A volume of 50 mL of the resulting dispersion of β-lactoglobulin micelles is then foamed by nitrogen sparging through a glass frit generating bubbles of 12-16 µm to produce a foam volume of 180 cm$^3$ using the standardized Foamscan™ (ITConcept) apparatus. The volume stability of the foam was then followed with time at 26° C. using image analysis and compared to the stability of the foam obtained with β-lactoglobulin treated in the same conditions, but without Arginine HCl, where no micelles were formed. Indeed, the foam volume stability is greatly improved by the presence of β-lactoglobulin micelles.

Example 8

Whey Based Fermented Dairy Product

Fermentation Trials

Material

Whey protein isolate (WPI) (Bipro®) was obtained from Davisco (Le Sueur, Minn., USA) (protein concentration 92.7%)

Spray dried whey permeate (Variolac 836): Lactose concentration: 83%-Minerals: 8%.

Lactic Acid 50%

Edible Lactose (Lactalis)

De-ionized water

Method

The Bipro® powder was dissolved in de-ionized water in order to have a protein concentration of 4.6%, i.e., for 3 liters of solution 154.5 g of WPI powder and 2845.5 g of water. The hydration time was 3 hours. After hydration, this solution has been divided in samples of 200 ml to prepare the different trials:

TABLE 3

| Trial | Whey permeate (%) | Lactose (%) | pH adjustment | Heating 85° C./ 15 min |
|---|---|---|---|---|
| 1 | 2.9 | 2.5 | 6.5 | + |
| 2 | 0 | 5 | 6 | + |
| 3 | 0 | 5 | 6.7 | − |
| 4 | 0 | 5 | 6.7 | + |
| 5 | 0 | 5 | 6.1 | + |
| 6 | 0 | 0 | 6 | + |
| 7 | 0 | 5 (added after pH adjustment) | 6 | − |
| 8 | 0 | 5 (added after pH adjustment) | 6 | + |

For each solution, lactic acid at 50% has been added to adjust the pH before heating.

Samples were heated with the double boiler up to 85° C. and maintain at this temperature during 15 minutes. After heating, solutions were cooled at 40° C. and inoculated with *Lactobacillus bulgaricus* and *Streptococcus thermophilus*. Samples were incubated 5 h 30 in a steam room at 41° C. before to be placed in a cold room at 6° C. The results are presented in Table 4.

TABLE 4

| Trial | Whey permeate | Lactose | pH | Heating | pH after 5 h30 | Aspect |
|---|---|---|---|---|---|---|
| 1 | + | + | 6.5 | + | 4.68 | Very firm |
| 2 | − | + | 6 | + | 4.7 | Firm |
| 3 | − | + | 6.7 | − | 5.78 | Liquid |
| 4 | − | + | 6.7 | + | 4.81 | Very firm |
| 5 | − | + | 6.1 | + | 4.59 | Very firm |
| 6 | − | − | 6 | + | 4.99 | Very firm |
| 7 | − | −added after pH adjustment | 6 | − | 4.87 | Liquid with white speckles |
| 8 | − | −added after pH adjustment | 6 | + | 4.77 | Firm |

Example 9

Whey Protein Boosted Ice Cream with Reduced Fat Content

Material

Whey protein isolate (WPI, PROLACTA® 90 from Lactalis, Retiers, France) with a protein content of 90%

Skim milk powder with 35% protein content

Sucrose

Maltodextrins DE39

Anhydrous milk fat

Emulsifier

De-ionised water

Edible hydrochloric acid 1M

Method

Using a double jacketed 80 L tank, the PROLACTA® 90 powder was dispersed at 50° C. in de-ionized water at a protein concentration of 9.67 wt % under gentle stirring in order to avoid foam formation, i.e., 3.3 kg of PROLACTA® 90 were dispersed in 31.05 kg of de-ionized water. After 1 hour of dispersion, the pH of the dispersion was adjusted to the micellization pH by addition of HCl. The temperature of the dispersion was raised to 85° C. and maintained for 15 minutes in order to generate the whey protein micelles. After 15 minutes, the temperature was decreased to 50° C. and the additional ingredients were sequentially added to the micelles dispersion (i.e., skim milk powder, maltodextrins DE39, sucrose, emulsifier and anhydrous milk fat). The final amount of mix was 50 kg with total solids content of 39.5% and a fat content of 5 wt %. After 30 minutes of hydration, the mix was two-step homogenized (80/20 bars) and pasteurized (86° C./30 s) before ageing during overnight. The day after, the ice-cream mix was frozen at an overrun of 100% using a Hoyer MF50 apparatus and hardened at −40° C. before storage at −20° C. The final ice cream contained 8 wt % proteins (20% caseins, 80% whey proteins) and 5 wt % fat on the ice cream mix basis.

Example 10

Powdered Whey Protein Micelles Obtained by Spray-Drying

Material

Whey protein isolate (WPI, PROLACTA® 90 from Lactalis, Retiers, France) with a protein content of 90%

Edible lactose

Maltodextrins DE39

De-ionised water

Edible hydrochloric acid 1M

Method

Using a double-jacketed 100 L tank, the PROLACTA® 90 powder was dispersed at 50° C. in de-ionized water at a protein concentration of 10 wt % under gentle stirring in order to avoid foam formation, i.e., 11 kg of PROLACTA® 90 were dispersed in 89 kg of de-ionised water. After 1 hour of dispersion, the pH of the dispersion was adjusted to the micellization pH (around 6.3 in that case) by addition of HCl. The temperature of the dispersion was raised to 85° C. and maintained for 15 minutes in order to generate the whey protein micelles. After 15 minutes, the temperature was decreased to 50° C. and the 10 wt % whey protein micelles dispersion was split in two batches of 50 kg. In a first trial, 20 kg of lactose were dispersed in 50 kg of micelles dispersion at 50° C. and stirred for 30 min. Similarly, 20 kg of maltodextrins DE39 were added to the remaining 50 kg of whey protein micelles dispersion.

The two mixtures were then spray dried into a NIRO SD6.3N tower at a flow rate of 15 L/h. The air input temperature was 140° C. and the air output temperature was 80° C. The water content of the obtained powders was lower than 5%. The size of the whey protein micelles was determined in presence of lactose and maltodextrin (DE39) in water using dynamic light scattering before and after spray drying. The total protein concentration was set to 0.4 wt % by dilution of the dispersion before spray drying or reconstitution of the powder in order to be in the dilute regime of viscosity for whey protein micelles. A Nanosizer ZS apparatus (Malvern Instruments) was used and micelle diameter was averaged from 20 measurements.

The particle diameter determined for whey protein micelles in presence of lactose and maltodextrins (DE39) was 310.4 nm and 306.6, respectively. After reconstitution of the powders, the respective diameters were found to be 265.3 nm and 268.5, respectively. These measurements confirm than whey protein micelles were physically stable regarding spray drying. The results were corroborated by TEM microscopy observations of 0.1 wt % whey protein micelles dispersions in water using negative staining in presence of 1% phosphotungstic acid at pH 7. A Philips CM12 transmission electron microscope operating at 80 kV was used. Whey protein micelles were observed in solution before spray drying and after reconstitution of the spray-dried powder. No difference of morphology and structure could be detected.

Example 11

Concentration by Evaporation

A whey protein isolate PROLACTA® 90 from Lactalis (lot 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 l/h. Pre-heating at 60° C. was followed by heat treatment of 85° C. for 15 minutes. Formation of whey protein micelles was checked by measurement of particle size using dynamic light scattering as well a turbidity measurement at 500 nm. The obtained 4% whey protein micelles dispersion was characterized by a hydrodynamic radius of particles of 250 nm, a polydispersity index of 0.13 and a turbidity of 80. The whey protein micelle dispersion was then used to feed a Scheffers evaporator at a flow rate of 500 l/h. The temperature and vacuum in the evaporator were adapted so that around 500 kg whey protein micelles concentrate having a protein concentration 20% were produced and cooled down to 4° C.

Example 12

Enrichment by Microfiltration

A whey protein isolate PROLACTA® 90 from Lactalis (lot 500648) has been reconstituted at 15° C. in soft water at a protein concentration of 4% to reach a final batch size of 2500 kg. The pH was adjusted by addition of 1M hydrochloric acid so that the final pH value was 5.90. The whey protein dispersion was pumped through plate-plate APV-mix heat exchanger at a flow rate of 500 L/h. A pre-heating at 60° C. was followed by heat treatment of 85° C. for 15 minutes.

Formation of whey protein micelles was checked by measurement of particle size using dynamic light scattering as well a turbidity measurement at 500 nm. The obtained 4% whey protein micelles dispersion was characterized by a hydrodynamic radius of particles of 260 nm, a polydispersity index of 0.07 and a turbidity of 80. The micelle form of the protein was also checked by TEM, and micelle structures with an average diameter of 150-200 nm were clearly visible. The whey protein micelle dispersion could be cooled at 4° C. for storage or directly used to feed a filtration unit equipped with a 6.8 m$^2$ Carbosep M14 membrane at a flow rate of 180 L/h. In that case, the concentration of the whey protein micelles was performed at 10° C. until the permeate flow rate reached 70 L/h. In that case, the final whey protein concentrate contained 20% of proteins. The structure of the micelles in the concentrate was checked by TEM, and clearly no significant change was visible compared to the 4% whey protein dispersion before microfiltration. Although the concentration of the whey protein micelles was performed at 10° C. in the present example, the concentration could also be performed at 55° C., or from about 60° C. to about 63° C.

Example 13

Whey Protein Micelles Powder Comprising at Least 90% Whey Protein 200 kg of a whey protein micelle concentrate obtained by microfiltration at 20% protein (see example above) were injected in a NIRO SD6.3N tower using an atomization nozzle (0=0.5 mm, spraying angle=65°, pressure=40 bars) at a product flow rate of 25 kg/h. The inlet temperature of product was 150° C. and the outlet temperature was 75° C. The airflow in the tower was 150 m$^3$/h. The moisture content in the powder was less than 4% and the powder was characterized by a very high flowability. Scanning electron microscopy of the powder exhibited very spherical particles having an apparent diameter ranging from 10 to 100 μm.

Example 14

Mixed Whey Protein Micelle Powder 20 kg of a whey protein micelle concentrate were mixed with 1.7 kg of maltodextrins with a DE of 39 so that the final whey protein micelle to maltodextrin ratio in powder is 70/30. This mixture was injected in a NIRO SD6.3N tower using an atomization nozzle (0=0.5 mm, spraying angle=65°, pressure=40 bars) at a product flow rate of 25 kg/h. The inlet temperature of product was 150° C. and the outlet temperature was 75° C. The airflow in the tower was 150 m$^3$/h. The moisture content in the powder was less than 4% and the powder was characterized by very high flow ability.

The powders of Examples 13 and 14, when reconstituted in water, comprise essentially micelles having the same structure and morphology as the whey protein micelle concentrate.

Example 15

Whey Protein Micelle Powder Obtained by Freeze-Drying

Material

Whey protein micelle concentrate at 20% protein produced by microfiltration in Example 12 with a protein content of 90%

Method 100 g of whey protein micelles concentrate were introduced in a plastic beaker and frozen at −25° C. for one week. This beaker was then placed in a lab-scale freeze drier Virtis equipped with a vacuum pump. Sample was left for 7 days until the pressure in the freeze drier remained constant at about 30 mbars. Around 20 g of freeze-dried whey protein micelles has been recovered.

Example 16

A Whey Protein Enriched Dark Chocolate without Sucrose

Material

| Ingredients | Percentage |
| --- | --- |
| Whey protein micelle powder from Example 13 with a protein content of 90% | 40-50% |
| Sucralose | 0.05-0.1% |
| Anhydrous milk fat | 3-5% |
| Cocoa liquor | 30-40% |
| Cocoa butter | 5-15% |
| Vanillin | 0.005-0.015% |
| Lecithin | 0.1-1% |

Method

Cocoa liquor is mixed with cocoa butter, butter fat, whey protein micelle powder, sucralose, vanillin and lecithin. This mixture is conched overnight at 65° C. until a homogenous paste is obtained. This chocolate mass is then molded in chocolate plates and cooled down. The dark chocolate is characterized by a final whey protein content of 45-50%.

Example 17

A Whey Protein Enriched White Chocolate

Material

| Ingredients | Method 1 | Method 2 | Method 3 |
|---|---|---|---|
| Whey protein micelle powder from Example 13 with a protein content of 90% | 15-25% | 25-35% | 35-40% |
| Sucrose | 40-45% | 30-35% | 30-35% |
| Anhydrous milk fat | 1-10% | 1-10% | 1-10% |
| Whey powder | 2-10% | 2-10% | 0% |
| Cocoa butter | 20-30% | 20-30% | 20-30% |
| Vanillin | 0.01-0.1% | 0.01-0.1% | 0.01-0.1% |
| Lecithin | 0.1-1% | 0.1-1% | 0.1-1% |

Method 1

Whey protein micelles, whey powder, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then molded in chocolate plates and cooled down. This white chocolate is characterized by a final whey protein content of 20%.

Method 2

Whey protein micelles, whey powder, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then molded in chocolate plates and cooled down. This white chocolate is characterized by a final whey protein content of 30%.

Method 3

Whey protein micelles, sucrose and vanillin are mixed and ground until the desired particle size distribution is obtained. This mixture is then conched overnight at 65° C. with cocoa butter, anhydrous milk fat and lecithin until a homogenous paste is obtained. This chocolate mass is then molded in chocolate plates and cooled down. This white chocolate is characterized by a final whey protein content of 30-35%.

Example 18

Aqueous Dispersion of Whey Protein Micelles Coated with Sulfated Butyl Oleate (SBO) or any Other Negatively Charged Emulsifier Material Whey protein micelle (WPM) powder from Example 13 with a protein content of 90%
SBO
Hydrochloric acid (1M)
Method WPM powder described in Example 13 is dispersed in MilliQ water to achieve a final protein concentration of 0.1 wt %. This dispersion is filtered on 0.45 μm filters in order to remove possible WPM aggregates. The pH of this WPM dispersion was brought down to 3.0 by addition of hydrochloric acid 1M. A 1 wt % dispersion of SBO is prepared at pH 3.0.

The hydrodynamic radius and zeta potential of these WPM was determined using the Nanosizer ZS apparatus (Malvern Instruments Ltd.). Diameter was 250 nm and electrophoretic mobility +2.5 $\mu m \cdot cm \cdot V^{-1} \cdot s^{-1}$. The hydrodynamic radius and electrophoretic mobility of the SBO dispersion at pH 3.0 are 4 nm and $-1.5/-2.0$ $\mu m \cdot cm \cdot V^{-1} \cdot s^{-1}$, respectively.

After having performed this preliminary characterization, the SBO dispersion is used to titrate the WPM one, while following evolution of hydrodynamic radius and electrophoretic mobility of the mixture. It was found that the hydrodynamic radius was constant around 250-300 nm until a WPM/SBO weight-mixing ratio of 5:1 was reached. At this point, the hydrodynamic radius diverges dramatically to 20000 nm and precipitation of complexes WPM SBO is encountered. Upon further addition of SBO, higher than a mixing ratio of 5:1, the hydrodynamic progressively decreased to 250 nm, as found initially for WPM, leveling of from a ratio of 4:1 on. Following the electrophoretic mobility of the mixture showed that it decreased upon addition of SBO, reaching zero value for a mixing ratio of 5:1. Then it continued to drop upon SBO addition, starting leveling of at $-3.0$ $\mu m \cdot cm \cdot V^{-1} \cdot s^{-1}$ from ratio 4:1 on.

The explanation for these results is that the positively charged WPM are, in a first step coated electrostatically with the negative head of the SBO until full charge neutralisation is achieved (mixing ratio 5:1). At this point, the hydrophobic tails from the SBO are able to self-associate, leading to over-aggregation with very large hydrodynamic diameter and precipitation of complexes. Upon further addition of SBO, the hydrophobic tails associate further to form a double coating, exposing their negative head to the solvent. This lead to negatively charged WPM with a double coating of SBO comparable to a full protein core liposome.

Similar results have been obtained with other acidic food grade emulsifiers such as DATEM, CITREM, SSL (from Danisco) in aqueous solution at pH 4.2 where they are mainly ionized in their anionic form (COO chemical functions).

Example 19

A Protein-Enriched Bechamel-Type Sauce

Material
Mixed whey protein micelle powder from Example 14 with a protein content of 70%
Butter
Flour
Skim milk
Salt
Method 30 g of mixed whey protein powder are dispersed in 1 liter of skim milk under heating. 30 g of butter and 80 g of flour are then added together with 2.85 g of salt. The mixture is then boiled in order to produce a bechamel-type sauce having a whey protein content of about 3 g/100 g.

Example 20

A Whey Protein-Enriched Base for Performance Bar

Materials

| Ingredients | Percentage |
|---|---|
| Mixed whey protein micelle powder from example 13 with a protein content of 90% (moisture 3.5%) | 40-50% |
| Brown rice syrup | 35-45% |
| Maltitol | 5-10% |
| Glycerol | 10-15% |

Method

Brown rice syrup is mixed with maltitol and glycerol at 25° C. Whey protein micelle powder is then added and mixing is performed for 10 minutes. A whey protein-enriched base for performance bar is then obtained and can be mixed with other ingredients (minerals, vitamins, flavors). This preparation contains more proteins than milk (38%).

Example 21

Determination of Repose Angle for Spray Dried Whey Protein Micelle Powder, Mixed Whey Protein Micelle Powder, Whey Protein Isolate Powder and Low Heat Skim Milk Powder Material Whey protein micelle powder from Example 12 with a protein content of 90% (moisture 3.5%)

Mixed whey protein micelle powder from Example 13 with a protein content of 90% (moisture 3.5%)

Whey protein isolate powder PROLACTA® 90 (lot 500658 from Lactalis, France; moisture 4%)

Low heat skim milk powder (lot 334314 from Emmi, Switzerland; moisture 3.5%)

Measuring device described to measure repose angle for powders according to ISO norm 4324

Method

The powder is placed in a funnel with a stem diameter of 99 mm and the powder is forced to flow using the agitator. The powder falls on a transparent plastic vessel with diameter 100 mm and a height of 25 mm. The angle of repose, $\Phi$, is measured from the following equation:

Repose angle $\Phi = \text{ARCTAN}(2h/100)$

Where h is the maximum height of the powder cone than can be obtained, all surface of the plastic vessel being covered with powder. Results from the repose angle test (values are mean of 3 measurements and standard deviation is indicated).

| | Whey protein micelle powder | Mixed whey protein micelle powder | Whey protein isolate | Low heat skim milk powder |
|---|---|---|---|---|
| Repose angle (°) | 24.6 ± 1.1 | 27.3 ± 0.7 | 34.3 ± 0.5 | 43.8 ± 2.8 |

Repose angle results clearly show that whey protein micelle powder, pure or mixed with maltodextrins, exhibit a significantly lower angle than the initial whey protein powder or even skim milk powder. A repose angle lower than 35° is characteristic of very well flowing powders.

Example 22

Recipes for Hollandaise-Type Sauce and Mayonnaise-Type Product Comprising Whey Protein Micelles Hollandaise-Type Sauce Mayonnaise-Type Sauce Hollandaise-Type Sauce

| Ingredients | % |
|---|---|
| Water | 80-90 |
| Binders | 1-10 |
| Acids | 0.1-5 |
| Whey protein micelles | 0.5-5 |
| Spices, salt, sugar, flavours, colorants | 5-10 |

Mayonnaise-Type Sauce

| Ingredients | % |
|---|---|
| Water | 75-85 |
| Binders | 1-10 |
| Acids | 1-10 |
| Whey protein micelles | 0.5-5 |
| Spices, salt, sugar, flavours, colorants | 5-15 |

Using whey protein micelles, it was possible to obtain fat-free products which have high acid and salt content. The advantage of having whey protein micelles is that the whitening effect is provided at the same time as the micelles being stable to the culinary matrix and the process treatment. The whey protein micelles further simulate the presence of fat by their emulsion properties.

Example 23

Co-spray-drying of WPM with wheat gluten hydrolysate (WGH) 2.2 kg of WPM powder was dispersed in 45.8 kg of demineralized water at 25° C. After 15 minutes stirring, the WPM dispersion was homogenized at 250/50 bars using a NIRO-SOAVI homogenizer at a flow rate of 50 kg·h$^{-1}$. The WGH (wheat gluten hydrolysate) powder (2 kg) (obtainable commercially or by standard methods known in the art) was then dispersed in the WPM dispersion (48 kg) so that the final solids content of the dispersions was 8% and the WPM to WGH weight ratio was 1:1. The final WPM content of the spray-dried powder was thus around 50%.

Example 24

Whey Protein Enriched Soup

Using a whey protein micelle powder according to the disclosure, a dry mix (28 g) was prepared using the following ingredients:

Broccoli Cream Soup

| Ingredients | grams |
|---|---|
| Whey protein micelles | 10-15 |
| Thickeners | 5-10 |
| Vegetable powder | 2-5 |
| Fat/oil | 1-5 |
| Salt | 0.5-3 |
| Spices, flavorings, flavor enhancers | 1-2 |

The product was reconstituted by addition of the dry mix into 250 mL of cold or hot water and boiled. The soup obtained has a creamy texture and a whey protein content of 4-6 g/100 g.

Example 25

Whey Protein Based Creamy Soup with Reduced Fat Content

Asparagus Cream Soup (29 g)

| Ingredients | grams |
|---|---|
| Whey protein micelles | 3-10 |
| Thickeners | 10-20 |

| Ingredients | grams |
|---|---|
| Vegetable powder | 1-5 |
| Fat/oil | 1-3 |
| Salt | 0.5-5 |
| Spices, flavorings, flavor enhancers | 1-2 |

The product is reconstituted by addition of the dry mix into 500 mL of cold or hot water and boiled in order to produce a soup with a creamy texture and appearance, and a reduced fat content.

Example 26

Co-Spray-Drying of Whey Protein Micelles with a Soup Base

A whey protein micelle dispersion was reconstituted by mixing 1.6 kg of whey protein micelles in 43.7 kg demineralized water. After 15 minutes stirring, the WPM dispersion was homogenized at 250/50 bars using a NIRO-SOAVI homogenizer at a flow rate of 50 kg·h$^{-1}$. Thereafter, 4.7 kg of soup base were added to the WPM dispersion. The final solids content of the dispersion was 12.6%. The dispersion was spray-dried. The product temperature at the output of the spray dryer was 75° C. and the final moisture content was 3.5%. The final WPM concentration in the powder was around 23%.

A typical dehydrated soup base obtainable by the process described above is given:

| Ingredients | Composition (g/100 g of WPM-Soup base powder) |
|---|---|
| Whey protein micelles | 20-30 |
| Thickeners | 20-40 |
| Salt, spices, flavorings, flavor enhancers | 3-9 |
| Cream | 5-15 |
| Maltodextrin | 10-20 |
| Vegetable oil | 3-8 |

Example 27

White Sauce Comprising Whey Protein Micelles

Using a WPM powder according to the disclosure, a dry mix (35 g) was prepared using the following ingredients:

| Ingredients | grams |
|---|---|
| Whey protein micelles | 3-10 |
| Thickeners | 20-40 |
| Salt, spices, flavorings, flavor enhancers | 1-9 |
| Fat/Oil | 1-4 |

The product was reconstituted by addition of the dry mix into 500 mL of cold water and boiled in order to produce a white sauce.

Example 28

Various concentrations of leucine were included in different compositions. Sensory testing was performed by Applicants to determine the ability of 26 participants to detect the presence of leucine in each of the concentrations of the different compositions. Initially, Applicants found that 23 of the 26 participants were able to detect 2 g of supplemental leucine in a flavored oral nutritional product with 99.9% confidence. The participants then described the product containing the leucine as "very bitter," and "tarter than other samples." Participants further stated that the product containing the leucine "taste[d] older and less fresh" than other samples, that the product "seem[ed] to burn a little," and that the product "[had] a bad taste."

Different compositions containing whey protein micelles and leucine were then prepared and further sensory testing was conducted by Applicants using the whey protein micelle and leucine compositions. The internal panelist sensory evaluation was conducted using a novel nutritional product developed by Applicants that comprised whey protein micelles and supplemental leucine. The concentrations of leucine in the products examined included 0.5, 1.0, 2.0 and 3.0 g L-leucine per serving. The results of this panel suggested that WPM could block the perceived bitterness of leucine at 1.0 and 2.0 g leucine, but that 0.5 and 3.0 g leucine were slightly more easily perceived by the panelists. Therefore, Applicants have surprisingly found that the protein micelles have the ability to hide the portion of the nutrient (e.g., leucine) that imparts bitterness to the composition.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of masking off-flavors of leucine in a composition, the method comprising: mixing a whey protein micelle powder and added leucine in a weight ratio of about 30:1 to about 1:100 to form a whey protein powder.

2. The method according to claim 1, wherein the whey protein powder comprises at least about 20% to at least about 80% whey protein micelles.

3. The method according to claim 1, wherein the whey protein powder comprises at least about 50% whey protein micelles.

4. The method according to claim 1, wherein the whey protein powder has a water binding capacity of at least about 50% to about 100%.

5. The method according to claim 1, wherein the total amount of leucine in the composition is between about 20% and about 40% by weight dry matter.

6. The method according to claim 1, wherein the dry weight ratio of added leucine to whey protein micelles is from about 1:2 to about 1:3.

7. The method according to claim 1, wherein the whey protein powder is obtained by a process selected from the group consisting of spray-drying and freeze-drying.

8. The method according to claim 1, the composition comprising at least one ingredient selected from the group consisting of an antioxidants, vitamins, minerals, phytonutrients, prebiotics, and probiotics.

9. The method according to claim 1, wherein the composition is a liquid, and the total amount of leucine in the composition is less than about 2.5 g per 100 g of the liquid, and the liquid is selected from the group consisting of water, water-based beverages, fruit juice, milk, and combinations thereof.

10. The method according to claim 9, the composition further comprising at least one ingredient selected from the group consisting of an antioxidants, vitamins, minerals, phytonutrients, prebiotics, and probiotics.

* * * * *